United States Patent
Rust

(10) Patent No.: US 11,484,554 B2
(45) Date of Patent: Nov. 1, 2022

(54) PANCREATIC CELLS FOR TREATING DIABETES AND METHODS OF GENERATING THE SAME

(71) Applicant: Seraxis, Inc., Germantown, MD (US)

(72) Inventor: William L. Rust, Germantown, MD (US)

(73) Assignee: Seraxis, Inc., Germantown, MD (US)

( * ) Notice: Subject to any disclaimer, the term of this patent is extended or adjusted under 35 U.S.C. 154(b) by 0 days.

(21) Appl. No.: 16/968,317

(22) PCT Filed: Feb. 8, 2019

(86) PCT No.: PCT/US2019/017281
§ 371 (c)(1),
(2) Date: Aug. 7, 2020

(87) PCT Pub. No.: WO2019/157329
PCT Pub. Date: Aug. 15, 2019

(65) Prior Publication Data
US 2021/0008122 A1    Jan. 14, 2021

Related U.S. Application Data

(60) Provisional application No. 62/628,470, filed on Feb. 9, 2018.

(51) Int. Cl.
*A61K 35/39* (2015.01)
*C12N 5/071* (2010.01)

(52) U.S. Cl.
CPC .......... *A61K 35/39* (2013.01); *C12N 5/0676* (2013.01); *C12N 2500/46* (2013.01); *C12N 2501/105* (2013.01); *C12N 2501/117* (2013.01); *C12N 2501/16* (2013.01); *C12N 2501/415* (2013.01)

(58) Field of Classification Search
CPC .................................................... A61K 35/39
See application file for complete search history.

(56) References Cited

PUBLICATIONS

NIH Stem Cell Guidelines (Year: 2016).*
Brevini et al., 2010, Theriogenology, vol. 74, pp. 544-550 (Year: 2010).*
Paris et al. (2010, Theriogenology, vol. 74, pp. 516-524) (Year: 2010).*
Munoz et al. (2008, Theriogenology, vol. 69, pp. 1159-1164) (Year: 2008).*
Gomez et al. (2010, Theriogenology, vol. 74, pp. 498-515) (Year: 2010).*
Jean et al. (2013, Develop. Growth Differ., vol. 55, pp. 41-51) (Year: 2013).*
Buta et al. (2013, Stem Cell Res., vol. 11, pp. 552-562) (Year: 2013).*
Lee et al., 2011, Int. J. Stem Cells, vol. 4(1), pp. 35-42 (Year: 2011).*
Konigshoff et al., 2011, EMBO Molecular Med., vol. 3, pp. 575-577 (Year: 2011).*
Ma et al., 2021, Frontiers in Endocrinology, vol. 11, pp. 1-11 (Year: 2021).*
International Search Report and Written Opinion dated Jun. 13, 2019, in PCT/US2019/017281.
Kumar et al., "Recent Developments in Beta-Cell Differentiation of Pluripotent Stem Cells Induced by Small and Large Molecules," International Journal of Molecular Sciences, Dec. 17, 2014, 15(12):23418-23447.
Nostro et al., "Efficient Generation of NKX6-1 Pancreatic Progenitors from Multiple Human Pluripotent Stem Cell Lines," Stem Cell Reports, Apr. 1, 2015, 4(4):591-604.
Pagliuca et al., "Generation of Functional Human Pancreatic [beta] Cells in Vitro," Cell, Oct. 9, 2014, 159(2):428-439.
Pezzolla et al., "Resveratrol Ameliorates the Maturation Process of beta-Cell-Like Cells Obtained from an Optimized Differentiation Protocol of Human Embryonic Stem Cells," PLoS One, Mar. 16, 2015, 10(3):e0119904, 21 pages.
Russ et al., "Controlled induction of human pancreatic progenitors produces functional beta-like cells in vitro," EMBO (European Molecular Biology Organization) Journal, Jul. 2, 2015, 34(13):1759-1772.
Southard et al., "Generation and selection of pluripotent stem cells for robust differentiation to insulin-secreting cells capable of reversing diabetes in rodents," PLoS One, Sep. 5, 2018, 13(9):e0203126, 21 pages, with 2 pages of corrections to Fig. 3 (Oct. 31, 2019).
Zhang et al., "Highly efficient differentiation of human ES cells and iPS cells into mature pancreatic insulin-producing cells," Cell Research, Apr. 1, 2009, 19(4):429-438.

* cited by examiner

*Primary Examiner* — Peter Paras, Jr.
*Assistant Examiner* — David A Montanari
(74) *Attorney, Agent, or Firm* — Foley & Lardner LLP

(57) ABSTRACT

The present disclosure provides cell-based compositions for treating diabetes, methods for identifying cells that preferentially differentiate into endoderm cells, and methods for preparing insulin-producing pancreatic cells, as well as related methods of use for treating diseases related to insulin deficiency.

7 Claims, 10 Drawing Sheets

Figure 1
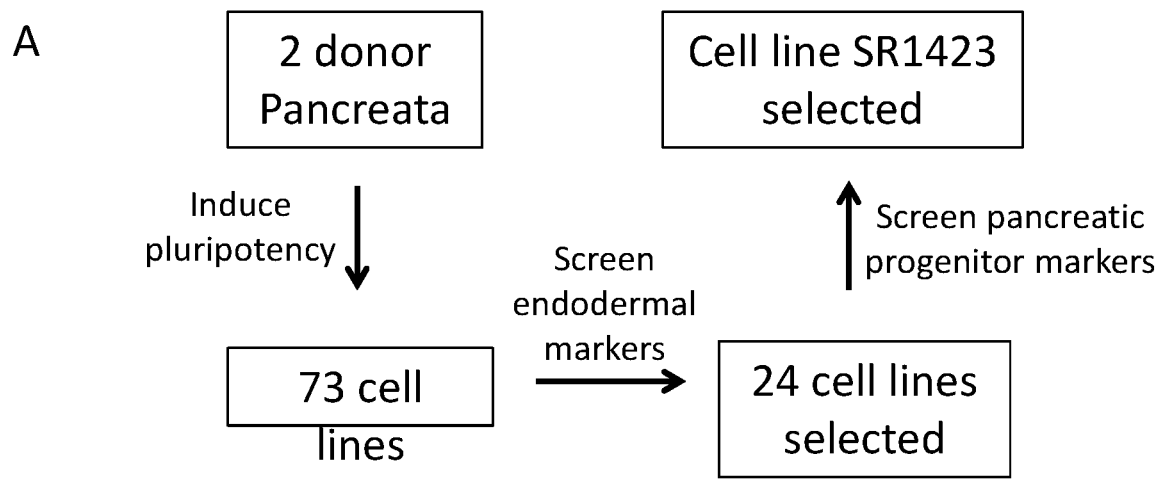
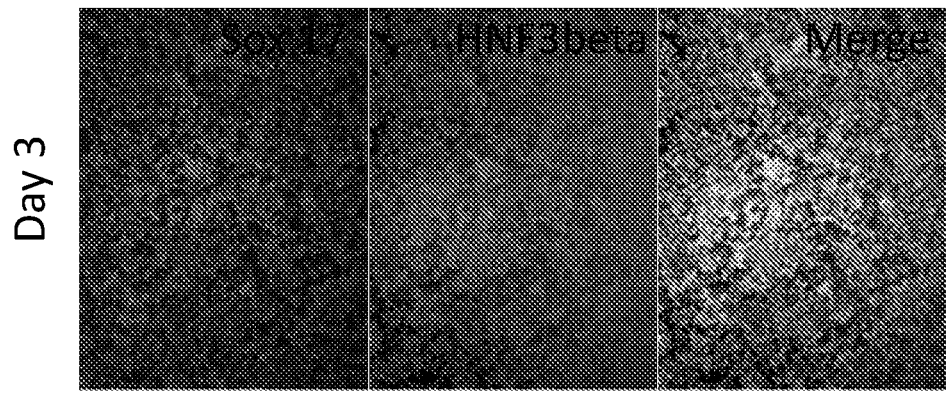
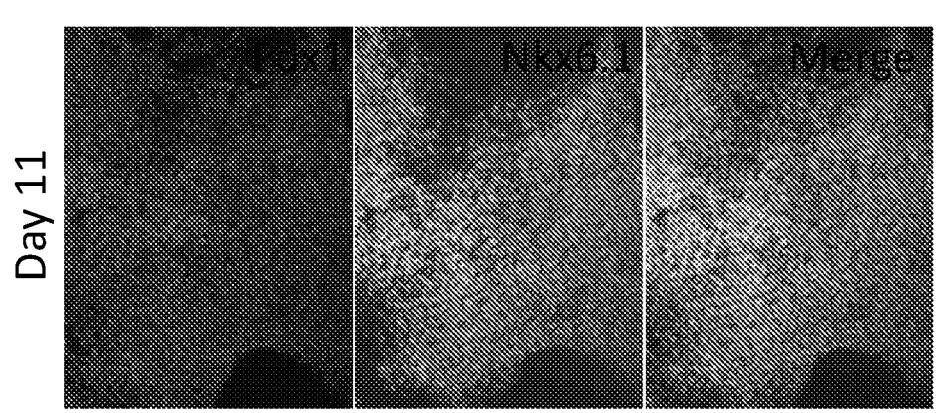

Figure 3
A.
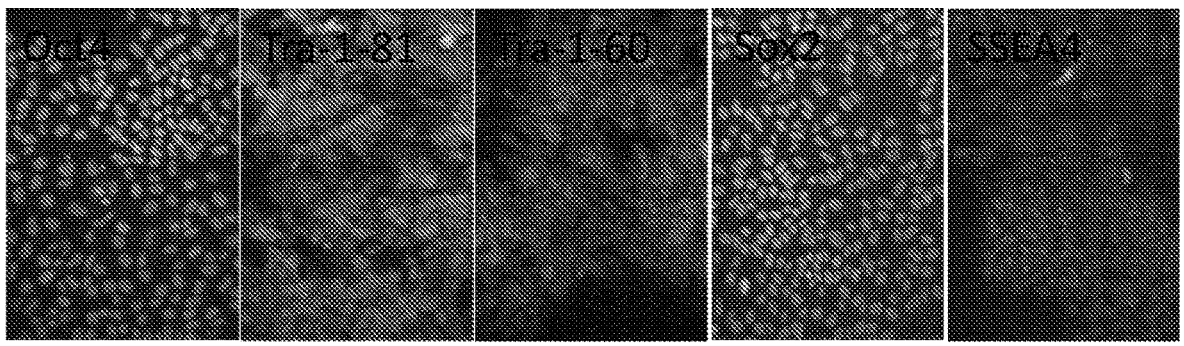
B.
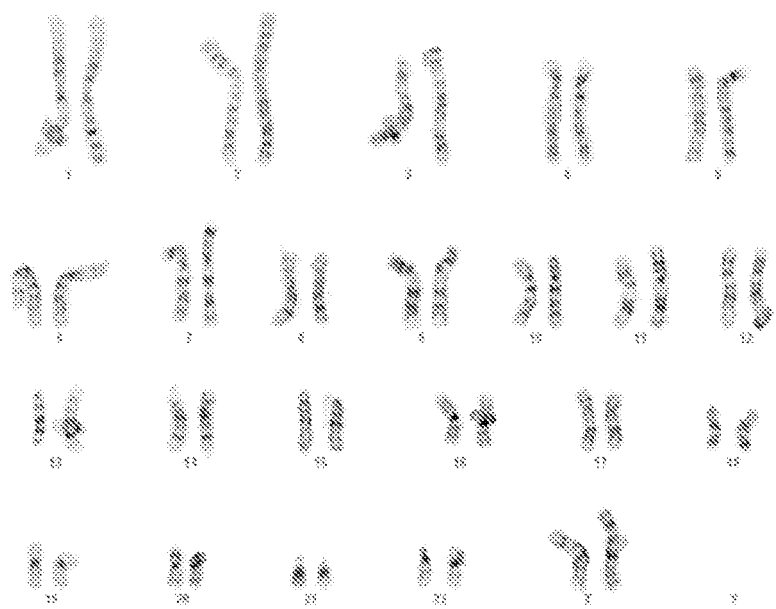
C.
DNA fingerprint
| Amelogenin | X | Y | D18S51 | 15 | 17 |
|---|---|---|---|---|---|
| vWA Penta E | 15 | 18 | Penta E | 7 | 15 |
| D8S1179 | 13 | | D5S818 | 11 | |
| TPOX | 9 | 12 | D13S317 | 12 | 13 |
| FGA | 22 | 25 | D7S820 | 10 | 13 |
| D3S1358 | 15 | 16 | D16S539 | 9 | 12 |
| THO1 C | 6 | 7 | SF1PO | 10 | 12 |
| D21S11 | 31 | | Penta | 11 | 13 |
D.
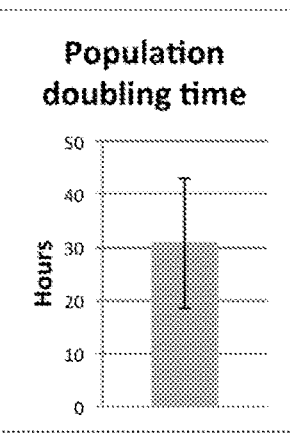

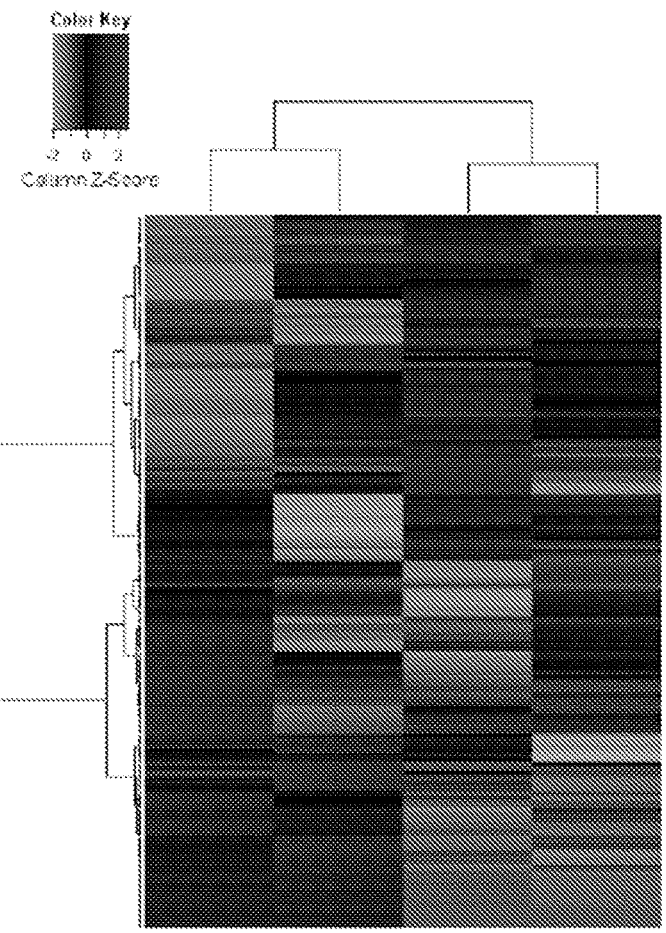

Agilent Human OneArray Plus

B.

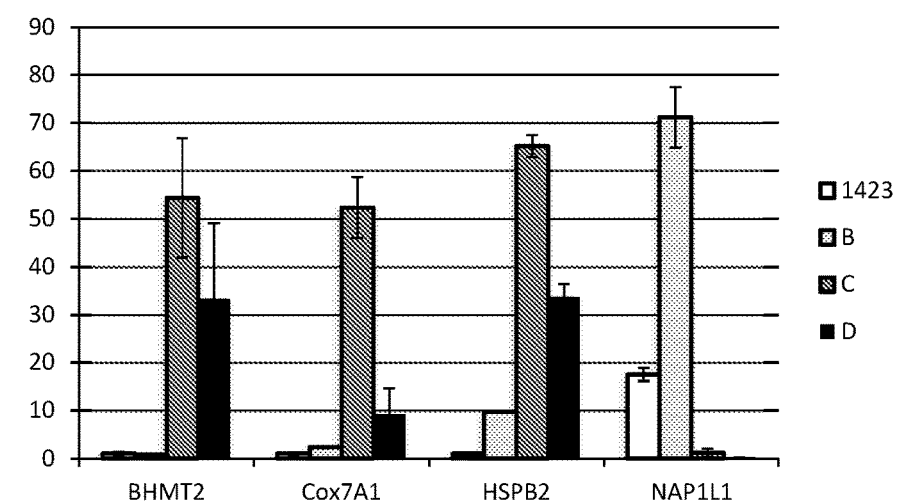

The correlation of expression profiles between samples and treatment conditions was demonstrated by unsupervised hierarchical clustering analysis.
Clustering was performed to visualize the correlations among the replicates and the differences between sample conditions. Up- and down-regulated genes are represented in red and green colors, respectively. A subset of differentially expressed genes was selected for this clustering analysis based on an intensity filter that pulls out genes with large expression differences between conditions. The top 250 genes passing this filter are represented above.

Figure 5
A.
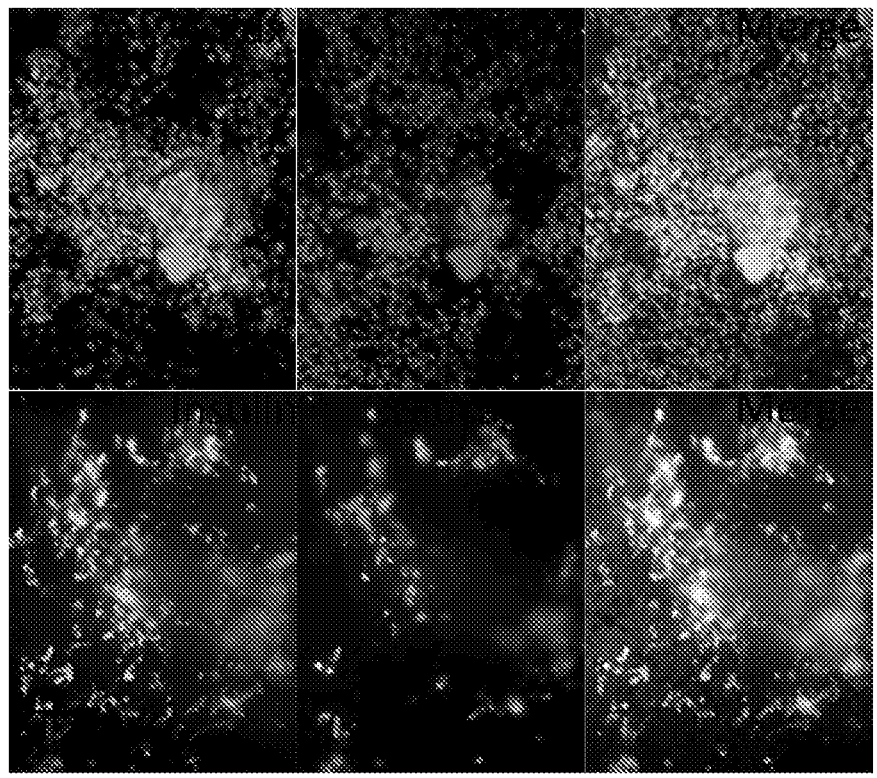
B.
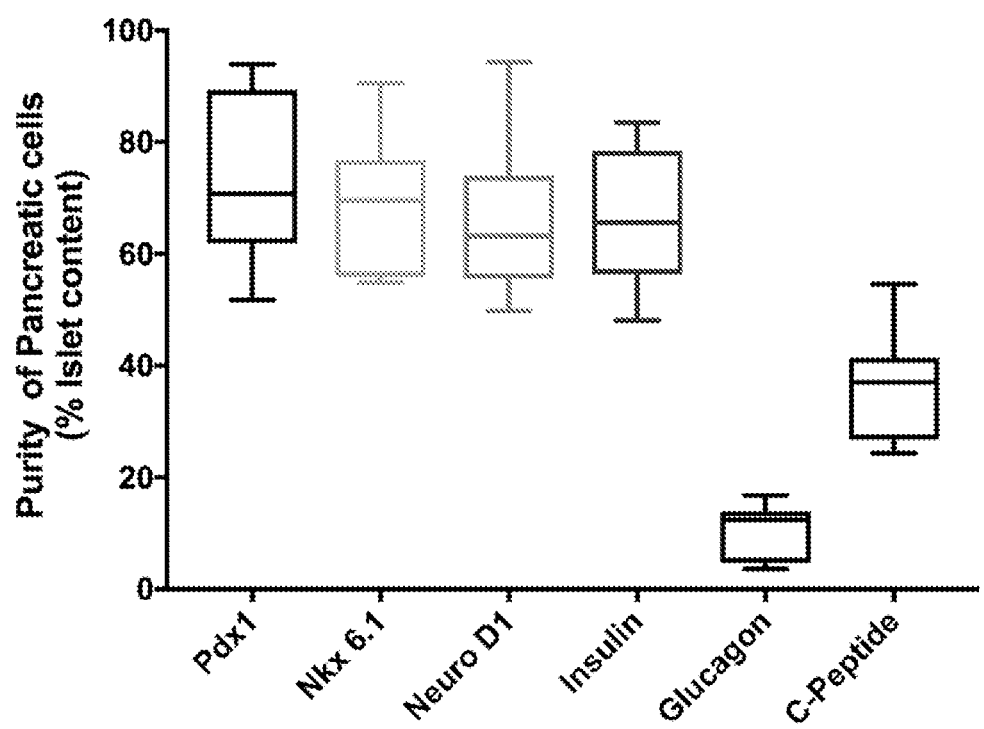

Figure 6
A.
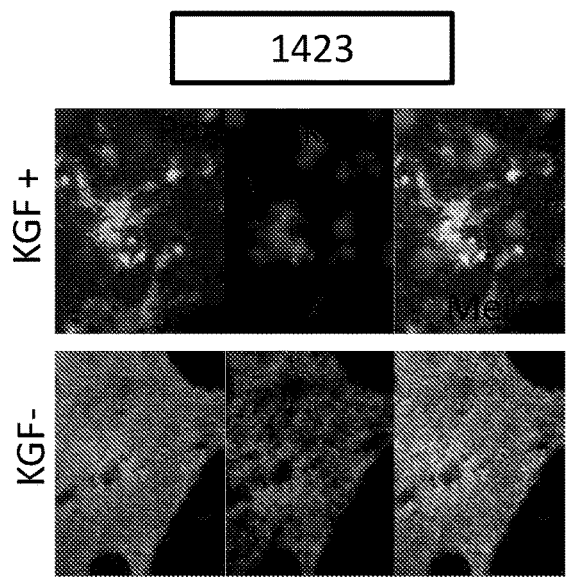
B.
Merge
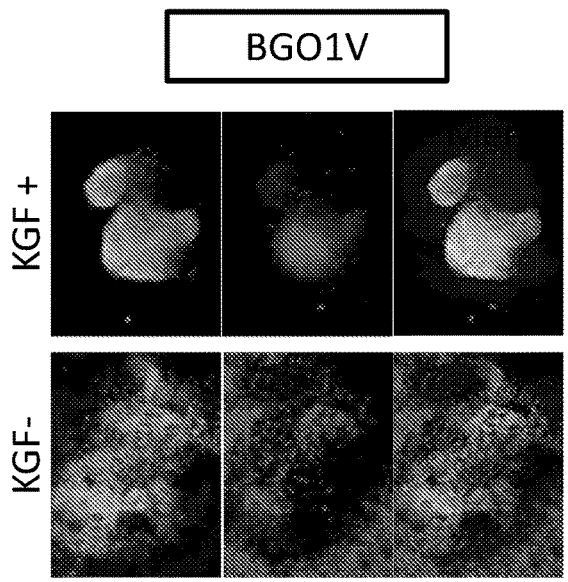
C.
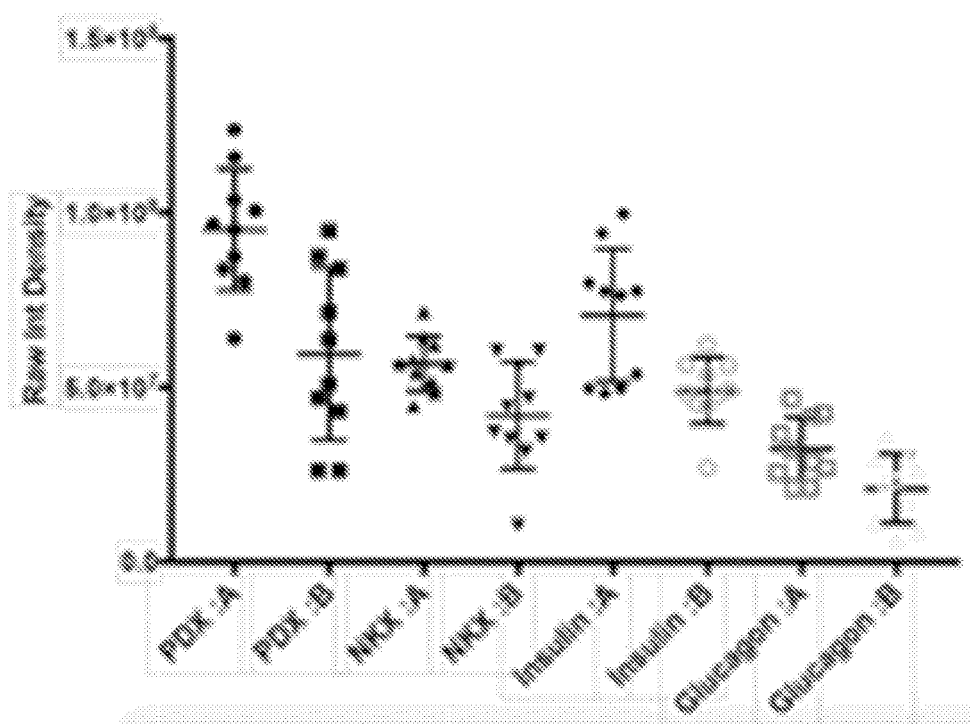

Figure 9
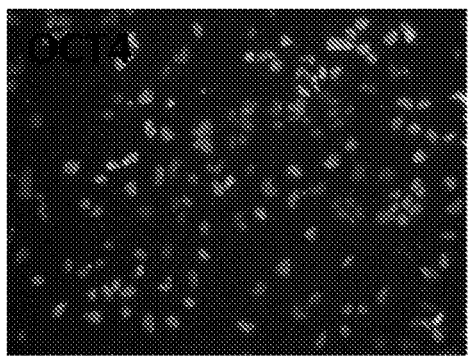
A.
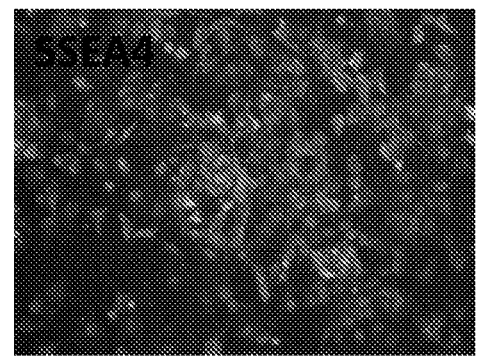
B.
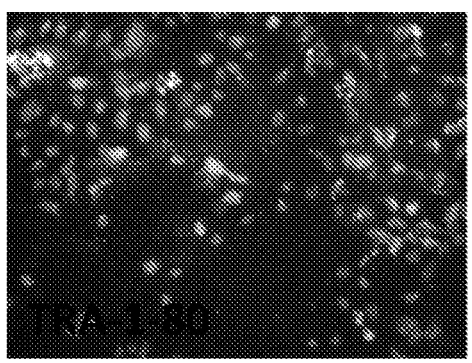
C.
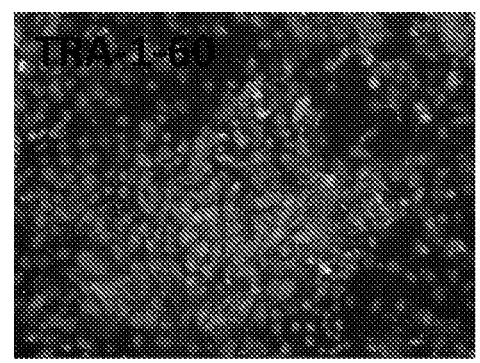
D.
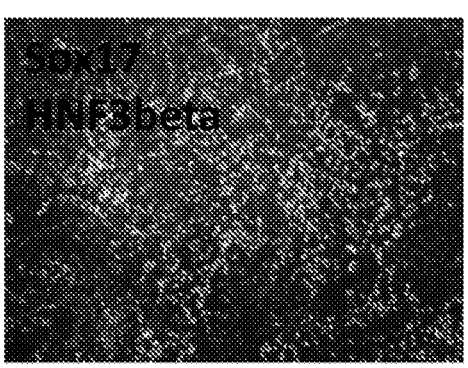
E.
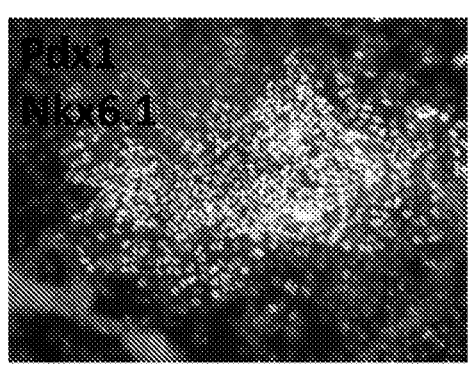
F.

Figure 10.
A.
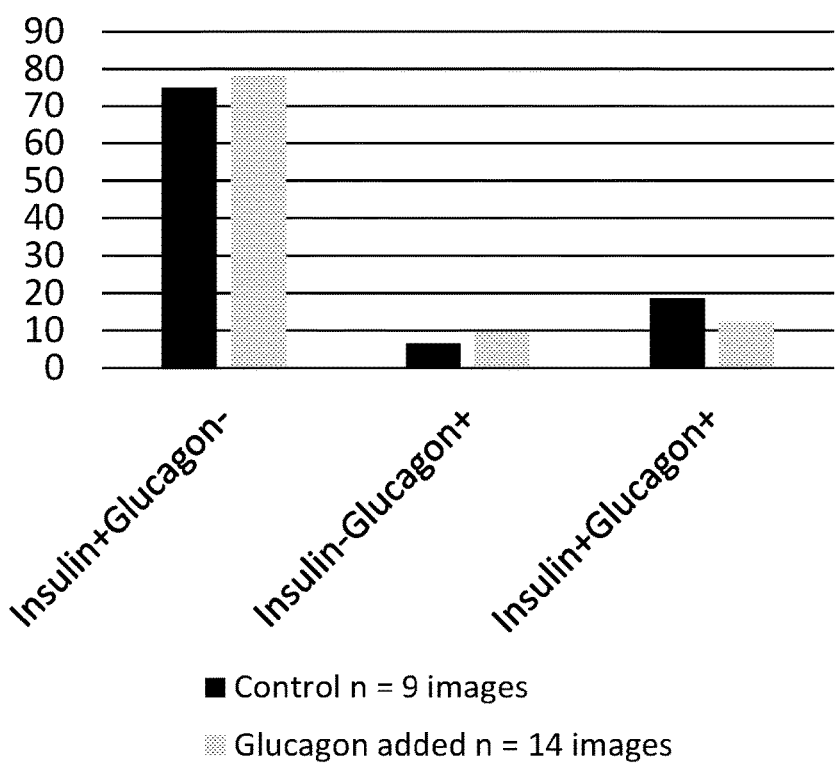
B.
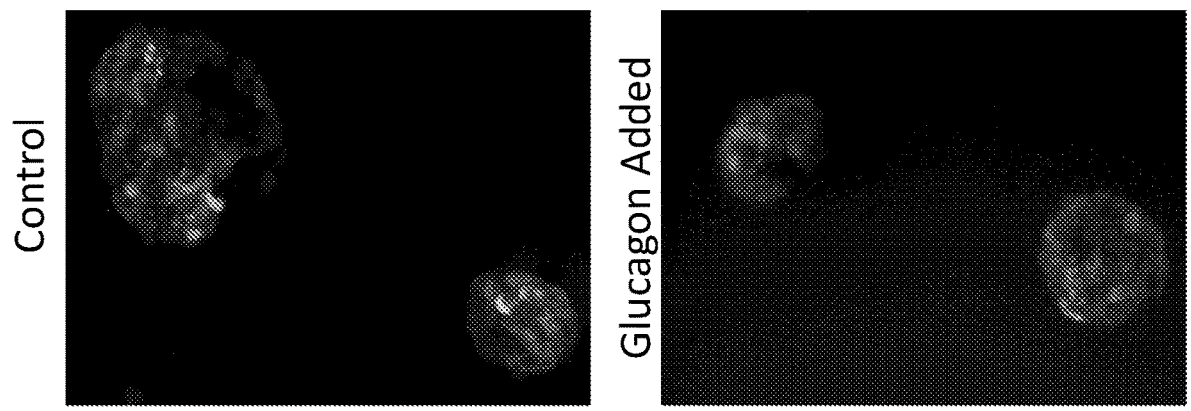

PANCREATIC CELLS FOR TREATING DIABETES AND METHODS OF GENERATING THE SAME

CROSS-REFERENCE TO RELATED APPLICATIONS

This application is the U.S. National Stage of PCT/US2019/017281, filed Feb. 8, 2019, which claims priority to U.S. Provisional Application No. 62/628,470, filed Feb. 9, 2018.

FIELD

The present disclosure relates generally to the field of cell biology, stem cells, and cellular differentiation. More specifically, this disclosure provides methods for generating pancreatic cells, methods of identifying cells for cell-based therapy, and related methods of use for treating diabetes.

BACKGROUND

The following discussion is provided to aid the reader in understanding the disclosure and is not admitted to describe or constitute prior art thereto.

Diabetes and Insulin

Diabetes mellitus (i.e., diabetes) is a disease in which the body's ability to produce or respond to the hormone insulin is impaired, resulting in abnormal metabolism of carbohydrates and elevated levels of glucose in the blood and urine. The disease is subdivided into several sub-types, described alternatively as Type diabetes mellitus, insulin-dependent diabetes mellitus (IDDM), mature onset diabetes of the young (MODY), latent adult diabetes (LADA), brittle diabetes, lean diabetes, Type 1.5, Type 2, Type 3, obesity-related diabetes, gestational diabetes, and other nomenclature accepted by the field.

In general, a subject with insulin-dependent diabetes is required to administer exogenous insulin to sufficiently lower blood glucose. A non-insulin-dependent subject may sufficiently lower blood glucose with pharmaceutical intervention including classes of drugs that enhance sensitivity to insulin, or excretion of glucose. A subject with insulin-dependent diabetes may benefit from a cell replacement therapy in which insulin-producing cells are implanted to the subject whether that disease is labeled as type 1, MODY, LADA, brittle, lean, Type 1.5, Type 2, Type 3, obesity related diabetes or any combination thereof.

Type I diabetes is usually diagnosed in children and young adults, and was previously known as juvenile diabetes. Only 5-10% of people with diabetes have this form of the disease. Mature onset diabetes is the most common form of the disease, and it arises due to the impairment or destruction of insulin-producing beta cells, development of insulin resistance, or both impairment of insulin-producing beta cells and development of insulin resistance. Diabetes can arise in non-obese adults and children due to a combination of genetic and environmental factors. In obese adults and children, the pancreas may attempt to make extra insulin in order to control blood glucose, but over time it is unable to keep up and maintain blood glucose at normal levels. The body may also become less sensitive to the insulin that is produced. Prolonged over-activity of the insulin-secreting beta cells may lead to beta-cell dysfunction and death.

Diabetes symptoms vary depending on how much a subject's blood glucose fluctuates. Some people, especially those with prediabetes or non-insulin dependent diabetes, may not experience symptoms initially. In Type I diabetes, symptoms tend to come on quickly and are more severe.

Some of the signs and symptoms of Type I and Type II diabetes include, but are not limited to, increased thirst; frequent urination; extreme hunger; unexplained weight loss; presence of ketones in the urine (ketones are a byproduct of the breakdown of muscle and fat that happens when there is not enough available insulin); fatigue; irritability; blurred vision; slow-healing sores; frequent infections, such as gums or skin infections and vaginal infections.

Cell-Based Therapies For Treating Diabetes

Insulin-dependent diabetes patients can potentially be cured with transplantation of new insulin producing cells, but this approach has been limited to date because these cells are hard to obtain in sufficient quantity and quality. See e.g. Pagliuca F W, et al. *Cell*, 154(2):428-439 (2014). It has, therefore, long been a goal of biomedical research to generate insulin producing beta cells from human stem cells in a more efficient and predictable manner. Id. To achieve this goal, protocols must be established that generate uniform beta cell populations that produce insulin when exposed to glucose. However, such a protocol has remained elusive. Numerous research groups have proposed various protocols that have produced varied results using different cell lines. This inconsistent production of functional beta cells increases the total cellular dose required in order to achieve therapeutic benefit, thus increasing the cost of a potential therapy and limiting clinical applicability due to variable results.

Most established protocols for generating insulin-producing beta cells from human stem yields highly variable cell populations. See e.g. Pagliuca F W, et al. *Cell*, 154(2):428-439 (2014). Indeed, it has been common practice in the field to tailor a given differentiation protocol to a specific cell line, thus preventing any standardization for differentiation within the art. Approaches to improve beta cell yield from various differentiation protocols has typically involved testing numerous combinations of factors that influence differentiation pathways in an iterative, trial-and-error type of approach. See e.g. Pagliuca F W, et al. Cell, 154(2):428-439 (2014); Rezenia A. et al. *Nat. Biotech.*, 32:1121-33 (2014); Schulz TC et al. Plos One, 7:e37004 (2012). Chetty S. et al. *Nat. Methods*, 10:553-556 (2012). Therefore, a particular protocol for making beta cells from one starting stem cell population may be ineffective for differentiating a different starting population.

Moreover, inconsistency within the resulting differentiated cell populations has impacted the clinical application of any proposed therapy, as researchers in this field have struggled to obtain differentiated populations with consistently high percentages of insulin-producing cells. This not only detracts from the potential efficacy of cell-based therapy to treat diabetes, but also raises concerns regarding the tumorigenic potential of cell transplants containing a population of heterologous cells. Additionally, low reproducibility between cell batches directly affects the cost of producing the cells and limits the translation of this protocol to the clinic.

Some of this variability in the employment of distinct differentiation protocols can be traced to the starting cell line. For example, it is shown that pluripotent cell lines can vary widely in their ability to differentiate to certain lineages. See, Bock C, et al. *Cell*, 144:439-452 (2011); Lim H, et al. *J. Vis. Exp.*, (90):e51755 (2014); Osafune K, et al. Nat. Biotechnol., 26:313-315 (2008). This varying capacity of individual human stem cells in their response to currently utilized differentiation protocols has proved to be a difficult obstacle to overcome, as researchers had no indication of the potential for a given cell line or starting cell to eventually yield therapeutic cells.

In addition, guidance provided from prior art may in fact be counter-productive when using a cell line with a slightly different genetic background. For example, a consistent feature of established protocols to generate insulin-producing cells from pluripotent stem cells is to limit the exposure to retinoic acid and cyclopamine. See Nostro et al. *Stem Cell Reports*, 4:1-14 (2015). Another consistent guidance from the prior art is that initiating differentiation in three-dimensional cultures in suspension is required for proper maturation of the pancreatic cells. See Pagliuca F W, et al. *Cell*, 154(2):428-439 (2014), Rezania et al. *Nature Biotechnology*, 32(11):1121-33 (2014). As discussed in more detail below, following such guidance may actually inhibit differentiation of insulin-secreting cells from various stem cell lines.

Thus, there remain needs for improved and predictable methods of generating therapeutic, insulin-producing cells for the treatment of diabetes. The present disclosure fulfills those needs.

SUMMARY

Described herein are cells and cellular compositions that produce insulin and may be used to treat diabetes, as well as methods of making and identifying the same.

In one aspect, the present disclosure provides methods of producing mammalian insulin-secreting cells, comprising: culturing mammalian stem cells in adhesion, thereby allowing the mammalian stem cells to spontaneously form three-dimensional structures; and culturing of the three-dimensional structures in suspension; wherein the culturing steps comprise at least a 20-day exposure to retinoic acid and cyclopamine, and do not comprise exposing the stem cells of three-dimensional structures to Wnt3A.

In another aspect, the present disclosure provides methods of producing insulin-secreting cells, comprising: culturing mammalian stem cells on an adhesive substrate in a first medium comprising Activin-A and Wortmannin, wherein the mammalian stem cells are not exposed to Wnt3a; further culturing the cells in at least one additional medium comprising retinoic acid and cyclopamine; and transferring the cells to a suspension culture when the cells form three-dimensional cell structures; wherein the cells are exposed to retinoic acid and cyclopamine for at least 20 days.

In some embodiments of the foregoing aspects, the mammalian stem cells may be human stem cells, while in some embodiments the mammalian stem cells may be non-human primate stem cells. In some embodiments of the foregoing aspects, the mammalian stem cells were derived from a cell line.

In one aspect, the present disclosure provides methods of producing mammalian insulin-secreting cells, comprising culturing mammalian stem cells in a first medium comprising an endoderm-inducing factor, thereby differentiating the mammalian stem cells into endoderm cells; and culturing the endoderm cells in a second medium comprising an endocrine-inducing factor, thereby differentiating the endoderm cells into endocrine cells; wherein the mammalian stem cells were not exposed to keratinocyte growth factors (KGF) prior to differentiation into endoderm cells.

In some embodiments, the mammalian stem cells may be human stem cells, non-human primate stem cells, or stem cells derived from another mammal, including but not limited to a pig, cow, sheep, horse, dog, or cat.

In some embodiments, the endoderm-inducing factor comprises Activin-A, retinoic acid, and/or cyclopamine. In some embodiments, the first medium may further comprise Wortmannin. In some embodiments, the first medium does not comprise Wnt3A. In some embodiments, the cells are cultured in the first medium for 1-3 days.

In some embodiments, the second medium may comprise noggin and/or KGF. In some embodiments, the second medium may comprise retinoic acid and cyclopamine. In some embodiments, the cells are cultured in the second medium for 1-4 days.

Some embodiments of this aspect may comprise further culturing the endocrine cells in a third medium comprising KGF, thereby differentiating the endocrine cells into pancreatic progenitor cells. In some embodiments, the third medium comprises noggin and/or epidermal growth factor (EGF). In some embodiments, the third medium comprises retinoic acid and cyclopamine. In some embodiments the cells are cultured in the third medium for 1-4 days.

Some embodiments of this aspect may comprise further culturing the pancreatic progenitor cells in a fourth medium comprising noggin, EGF, γ-secretase inhibitor XXI, and/or Alk5i II. In some embodiments, the fourth medium may comprise T3. In some embodiments, the fourth medium may comprise retinoic acid and cyclopamine. In some embodiments, the cells are cultured in the fourth medium for 1-4 days.

Some embodiments of this aspect may comprise further culturing the pancreatic progenitors in a fifth medium comprising Alk5i II and/or retinoic acid. In some embodiments, the fifth medium may comprise T3. In some embodiments, the fifth medium may comprise retinoic acid and cyclopamine. In some embodiments, the cells are cultured in the fifth medium for 1-5 days.

Some embodiments of this aspect may comprise further culturing the pancreatic progenitors in a sixth medium comprising Alk5i II, nicotinamide, and/or insulin-like growth factor (IGF)-I. In some embodiments, the sixth medium may comprise T3 and/or BMP4. In some embodiments, the sixth medium may comprise retinoic acid and cyclopamine. In some embodiments, the sixth medium may comprise glucagon. In some embodiments, the cells are cultured in the sixth medium for 1-9 days.

In another aspect, the present disclosure provides methods of producing insulin-secreting pancreatic cells, comprising culturing human stem cells in a first medium comprising Activin-A and Wortmannin, thereby differentiating the human stem cells into endoderm cells, wherein the human stem cells were not exposed to keratinocyte growth factors (KGF) prior to differentiation into endoderm cells; and culturing the endoderm cells in a second medium comprising retinoic acid and cyclopamine, thereby differentiating the endoderm cells into endocrine cells; culturing the endocrine cells in a third medium comprising KGF, noggin, and EGF, thereby differentiating the endocrine cells into pancreatic progenitor cells; and culturing the pancreatic progenitor cells in a fourth medium comprising noggin, EGF, γ-secretase inhibitor XXI, and Alk5i II, thereby differentiating the pancreatic progenitor cells into insulin-producing pancreatic cells.

In some embodiments of this aspect, the second culture medium further comprises KGF. In some embodiments, the human stem cells are derived from pancreatic primary tissue. In some embodiments, the fourth medium may comprise a thyroid hormone, such as T3.

In some embodiments of this aspect, both the third and fourth mediums may comprise retinoic acid and cyclopamine.

Some embodiments of this aspect may comprise further culturing the cells in a fifth and/or sixth medium, wherein the fifth medium comprising Alk5I II and retinoic acid, and optionally cyclopamine and wherein the sixth medium comprising Alk5i II, nicotinamine, IGF-I, and optionally retinoic acid and cyclopamine. In some embodiments, the sixth medium may comprise glucagon.

In some embodiments of the foregoing aspects, the cells may be cultured for 30 days or less.

In another aspect, the present disclosure provides cell-based compositions for treating diabetes, comprising a population of surrogate pancreatic cells and a suitable carrier for implantation into a human subject in need thereof, wherein at least 66% of the surrogate pancreatic cells are insulin-producing pancreatic cells.

In some embodiments, at least 66% of the surrogate pancreatic cells express NeuroD1, while in some embodiments, at least 68% of the surrogate pancreatic cells express Nkx6.1.

In some embodiments, the insulin-producing pancreatic cells were derived according to a method comprising culturing a population of human stem cells on an adhesive substrate in a first medium comprising an endoderm-inducing factor, wherein the mammalian stem cells are not exposed to Wnt3a; further culturing the cells in at least one additional medium comprising retinoic acid and cyclopamine; and transferring the cells to a suspension culture when the cells form three-dimensional cell structures; wherein the cells are exposed to retinoic acid and cyclopamine for at least 20 days.

In some embodiments, the endoderm-inducing factor comprises Activin-A and/or Wortmannin. In some embodiments, the at least one additional medium may comprise KGF, noggin, EGF, and/or a thyroid hormone, such as T3.

In some embodiments, the surrogate pancreatic cells may be encapsulated in a macro-capsule. For example, the cells may be encapsulated in a macro-capsule comprising alginate, cellulose sulfate, glucomannan, or a combination thereof.

In some embodiments of the foregoing aspects, the human stem cells are derived from pancreatic primary tissue, are human embryonic stem cells, are induced pluripotent stem cell, or are reprogrammed cells that are not pluripotent. In some embodiments, the reprogrammed cells are derived from pancreatic primary tissue, for example, by expressing reprogramming genes without incorporating the reprogramming genes into the genome of the cell. In some embodiments, the reprogramming genes may be encoded on at least one episomal expression plasmid, which does not incorporate into the genome. In some embodiments, the reprogramming genes comprise Oct4, Sox2, Klf4, and L-Myc.

In another aspect, the present disclosure provides methods of identifying undifferentiated cells that preferentially differentiate into an endodermal lineage, comprising assessing expression of BHMT2 and NAP1L1 in an undifferentiated cell and identifying the cell as having a preference for differentiating into an endodermal lineage if BHMT2 expression is down-regulated relative to a control cell and NAP1L1 expression is up-regulated relative to a control cell.

Some embodiments of this aspect further comprise assessing the expression of Cox7A1 and HSPB2 in the undifferentiated cell and identifying the cell as having a preference for differentiating into an endodermal lineage if both Cox7A1 and HSPB2 expression are down-regulated relative to a control cell. In some embodiments, the control cell may be a pluripotent cell that does not exhibit preferential differentiation to the endodermal lineage or a substantial inability to differentiate to the mesodermal lineage.

In some embodiments, BHMT2 expression is down-regulated at least 2 logs relative to the control cell and NAP1L1 expression is up-regulated at least 2 logs relative to the control cell when the assessed undifferentiated cell preferentially differentiates into an endodermal lineage. In some embodiments, both Cox7A1 and HSPB2 expression are down-regulated at least 2 logs relative to the control cell when the assessed undifferentiated cell preferentially differentiates into an endodermal lineage.

Some embodiments of this aspect further comprise assessing expression of GLIS2, CCDC58, MTX3 and C7orf29. For example, in some embodiments, GLIS2, CCDC58, and MTX3 expression may be up-regulated relative to the control cell and C7orf29 expression may be down-regulated relative to the control cell when the assessed undifferentiated cell preferentially differentiates into an endodermal lineage.

In some embodiments, the level of expression is assessed by Q-PCR and/or by microarray analysis.

The following detailed description is exemplary and explanatory, and is intended to provide further explanation of the invention.

BRIEF DESCRIPTION OF THE DRAWINGS

FIGS. 1A-1C show selection of the induced pluripotent stem cell (iPSC) line SR1423 from the islet of Langerhans. FIG. 1A shows the selection scheme of SR1423. FIG. 1B represents immunostaining followed by fluorescent microscopy to show SR1423 expression of endoderm markers Sox17 (left) and HNF3beta (center) on Day 3 of differentiation. FIG. 1C shows immunostaining of pancreatic markers Pdx1 (left) and Nkx6.1 (center) on Day 11 of differentiation of SR1423 cells. Merged images shows co-staining of the markers combined with a nuclear stain. The images are taken with 40× magnification.

FIGS. 3A-3D show that SR1423 cells possess characteristics typical of pluripotent stem cells. FIG. 3A shows that the SR1423 cells express the pluripotency markers Oct4, Tra-1-81, Tra-1-60, Sox2, SSEA. FIG. 3B shows that the karyotype of the SR1423 cells after 40 passages in culture is normal. FIG. 3C shows that the DNA fingerprint as assessed by single tandem repeat analysis (STR). FIG. 3D shows SR1423 cell doubling time.

FIG. 4A-4B shows that SR1423 cells have a gene expression pattern correlating with preferential differentiation to the endodermal lineage. FIG. 4A shows a gene expression profile cluster analysis of SR1423, B, C, and D. The correlation of expression profiles between two lines that demonstrate preferential differentiation to endoderm (SR1423 and B) and two lines that do not show preferential differentiation (C, D) was demonstrated by unsupervised hierarchical clustering analysis. Up regulated genes are shown in red and down regulated genes are shown in green. A subset of differentially expressed genes was selected from this clustering analysis based on an intensity filter that identifies genes with large expression differences between conditions. The 250 genes with the largest expression differences are represented. FIG. 4B qRT shows PCR verification of a subset of up and down regulated genes identified in A.

FIGS. 5A-5B show that SR1423 cells yields robust pancreatic, hormone secreting cell populations. FIG. 5A shows SR1423 differentiation after 28 days with immunostaining for Pdx (left), Nkx6.1 (center) and merge (right) in the upper row. The lower row shows immunostaining for insulin (left), glucagon (center), and merge (right). "Merge" images include nuclear stain. All images were taken after 28 days of differentiation under 40× original magnification (n=10). FIG.5B shows quantification of average purity of pancreatic cells in population. 68% of the cells were found to express Nkx6.1 and 66.5% were expressing insulin.

FIGS. 6A-6C show that differentiation can be improved across multiple cell lines by excluding KGF. FIG. 6A shows immunofluorescence staining of Pdx (left) and Nkx6.1 (center) of SR1423 cells after differentiation with or without KGF. FIG. 6B shows immunofluorescence staining of Pdx (left) and Nkx6 (center) of BGO1V cells after differentiation with or without KGF. FIG. 6C compares the disclosed protocol to a published protocol that exposes early endoderm cells to KGF in HDC57 and BGO1V cells. Expression levels were measured by Raw Integrated density (n=10) and compared the −KGF protocol and +KGF protocol. Images were collected at 40× magnification. Error bars represent the MeanSD; *P<0.05; ****P<0.0001; ns, not significant.

FIGS. 9A-9F show a representative example of a stem cell line derived from non-human primate (NHP) tissue. The undifferentiated line A1.3 from NHP donor A expresses the pluripotency marker Oct4, SSEA4, Tra-1-80 and Tra-1-60 (A-D). These cells express the endodermal markers Sox17 and HNF2beta on day 4 of differentiation (E), and the pancreatic markers Pdx1 and Nkx6.1 on day 12 (F). The nuclei of the cells are stained.

FIGS. 10A-B show that exposure to glucagon reduces the amount of cells that co-express insulin and glucagon

DETAILED DESCRIPTION

Figure 2:
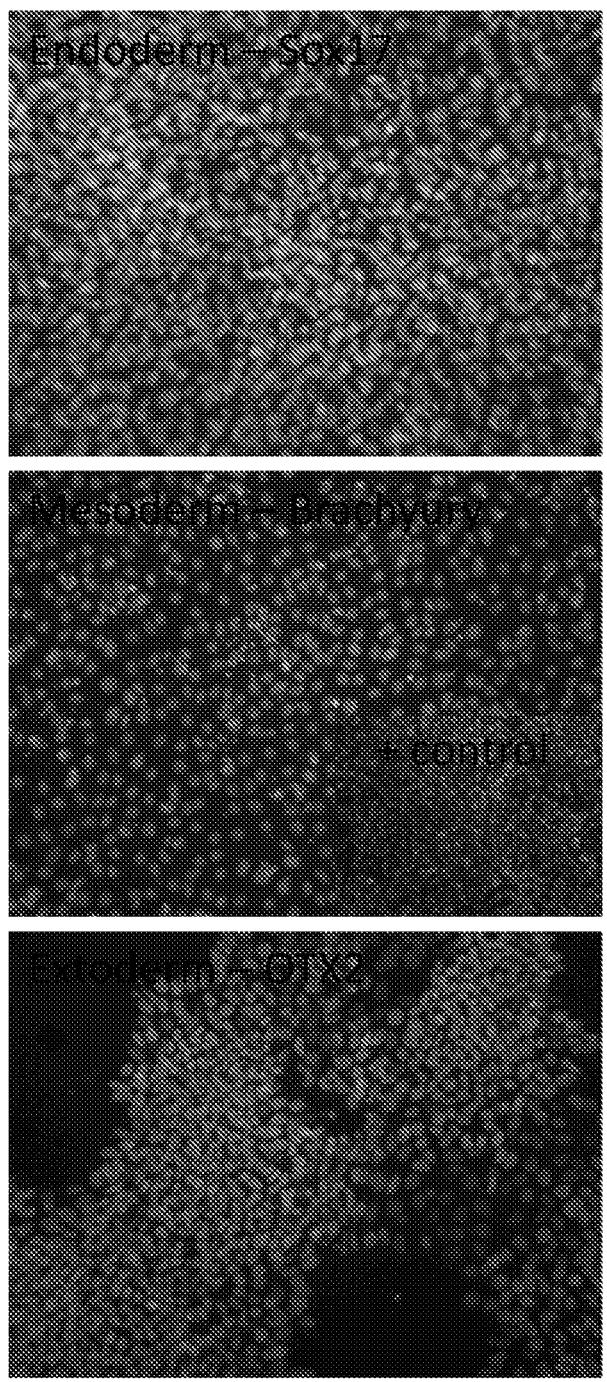
FIG. 2 shows that the SR1423 cells differentiate poorly into the mesodermal lineage. The SR1423 were immunostained for Sox17 (endoderm), Brachyury (mesoderm), or OTX2 (ectoderm). The nuclear stain (apparent in the mesoderm frame) shows total cells number. The figure demonstrates that SR1423 cells have a capacity to become endoderm and ectoderm (as indicated by the nearly uniform labeling of Sox17 and Otx2), but differentiate poorly into mesoderm, as indicated by a failure to express Brachyury.

Described herein are insulin-secreting cells that can be used to treat diabetes and improved methods of generating pure therapeutic cell populations of human insulin-producing beta cells. More specifically, the present disclosure provides methods of producing mammalian insulin-secreting cells, comprising initiating cultures with a stem cell line that has a preference or predisposition to differentiate to the endodermal lineage, such that a simple differentiation protocol can yield a pure population of insulin-secreting cells that display the mature phenotype of secreting insulin in response to glucose. The disclosed protocol may include, among other steps, exposing stem cells (in particular, stem cells that exhibit a preference or predisposition toward an endoderm lineage) long-term (e.g., at least 20 days) to retinoic acid and cyclopamine (or chemical analogs). The cultures may be initiated in adhesion, allowing the cells to naturally and spontaneously form three-dimensional structures; and then transferring the three-dimensional structures to suspension culture. The cells may not be exposed to Wnt3a during culture, either while grown in adhesion or in suspension. Additionally, this disclosure also provides methods for identifying a population of cells that are suitable for cell therapy and which possess a predisposition for differentiating toward an endodermal lineage.

I. Definitions

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the term "substantially free of" will refers to that the agent the composition is substantially free of has not been added, but it does not exclude that trace amounts exists of the agent.

As used herein, the term "islet cell" refers to terminally differentiated pancreatic endocrine cells, and any precursor cell that is committed to form progeny normally classified as pancreatic endocrine. The islet cell exhibits some of the morphological features and phenotypic markers (exemplified below) typical of an islet cell lineage. Mature alpha cells secrete glucagon; mature beta cells secrete insulin; mature delta cells secrete somatostatin; PP cells secrete pancreatic polypeptide.

As used herein, "pancreatic progenitors," "pancreatic precursors," or "pancreatic stem cells" are pancreatic or islet cells that do not meaningfully secrete endocrine hormones, but those cells can proliferate and generate terminally differentiated cells capable of secreting endocrine hormones (e.g., insulin). Early pancreatic progenitors are multipotent, which means that they are capable of forming at least pancreatic endocrine and pancreatic exocrine cells.

As used herein, the term "stem cells" denotes undifferentiated cells that are able to differentiate into specialized cells (e.g., insulin-producing pancreatic cells). For the purposes of this application, the term "stem cell" can include pluripotent cells derived from pre-embryonic, embryonic, or fetal tissue after fertilization that are capable of producing progenitors of all of the three germinal layers (i.e., endoderm, mesoderm, and ectoderm); induced pluripotent cell (i.e., cells that have been transduced with reprogramming genes) and are capable of producing progenitors of all of the three germinal layers; and multipotent cells, such as reprogrammed cells (i.e., cells that have been transduced with reprogramming genes) that can differentiate into only one or two germ layers or that preferential differentiate into a certain germ layer (e.g., reprogrammed cells that preferentially differentiate into ectoderm or endoderm cell types). The term includes both established lines of stem cells of various kinds (including cells obtained from primary tissue) that are pluripotent or multipotent in the manner described.

As used herein, the terms "induced pluripotent cells" or "induced pluripotent stem cells" ("iPS cells") denote pluripotent cells derived by reprogramming of adult somatic cells, reproductive cells, pluripotent cells, or other cell types, following standard art accepted methods (e.g., somatic-cell nuclear transfer, transduction with reprogramming genes, chemical inducement (see De Los et al., *Cell Research*, 23:1337-1338 (2013); Federation et al., *Trends in Cell Biology*, 24:179-187 (2013)), etc.). The term includes both established induced pluripotent stem cells, and cells obtained from primary tissue that are pluripotent in the manner described.

As used herein, the terms "non-pluripotent reprogrammed cells" or "multipotent reprogramed cells" denote cells derived by reprogramming of adult somatic cells, reproductive cells, pluripotent cells, or other cell types, with known reprogramming methods, such as transduction/expression of reprogramming genes and other methods discussed above. Unlike induced pluripotent cells, "non-pluripotent reprogrammed cells" or "multipotent reprogramed cells" may differentiate into only one or two germ layers or possess a preference to differentiate into a certain germ layer (e.g., reprogrammed cells that preferentially differentiate into ectoderm or endoderm cell types, but which cannot efficiently differentiate into mesoderm cell). The term includes both established induced multipotent cells (e.g., SR1423), and cells obtained from primary tissue that are reprogrammed to be multipotent in the manner described.

As used herein, the term "reprogramming genes" denotes known genes and transcription factors that are commonly used in the art to induce pluripotency or multipotency in differentiated cells. Exemplary reprogramming genes include, but are not limited to, Oct4 (i.e., Oct-3/4 or Pou5f1); Sox family transcription factors such as Sox1, Sox2, Sox3, Sox15, and Sox18; Klf family transcription factors such as Klf4, Klf1, Klf2, and Klf5; Myc family transcription factors such as C-myc, N-myc, and L-myc; Nanog; LIN28; and Glis1. Those of skill in the art will understand that the disclosed reprogramming genes, as well as other reprogramming genes known in the art may be combined in various ways in order to induce pluripotency or multipotency. For example, Yu et al., Science, 318(5858):1917-20 (2007) demonstrated that a combination of LIN28, Oct4, Sox2, and Nanog can be used to generate iPS cells, while Maekawa et al., Nature, 474(7350):225-29 (2011) demonstrated that a combination of Glis1, Oct-3/4, Sox2, and Klf4 can be used to generate iPS cells.

As used herein, the term "differentiate" or "differentiation" denotes a change in cell type from a less specific cell to a more specific cell. For example, any cell that has exited the pluripotent state and progressed along a developmental pathway toward a defined germ line has undergone differentiation. The term "differentiated" is a relative term, so differentiating cells can be at different stages during their developmental path towards a mature functional cell type. A cell at a later stage of developmental progression can therefore be said to be more differentiated than a cell at an earlier stage.

As used herein, "differentiation inducing factors", as used in this disclosure, refers to one of a collection of compounds that are used in culture systems of this invention to induce differentiation of stem cells to differentiated cells of the islet lineage (including precursor cells and terminally differentiated cells). No limitation is intended as to the mode of action of the compound. For example, the agent may assist the differentiation process by inducing or assisting a change in phenotype, promoting growth of cells with a particular phenotype or retarding the growth of others. It may also act as an inhibitor to other factors that may be in the medium or synthesized by the cell population that would otherwise direct differentiation down the pathway to an unwanted cell type. Within the category of "differentiation inducing factors" a person of ordinary skill in the art will understand that certain factors are known to induce certain steps throughout the differentiation process. For instance, a person of ordinary skill in the art would understand that an "endoderm-inducing factor" can include, but is not limited to, Activin-A, and/or Wortmannin, either alone or in combination. Similarly, an "endocrine-inducing factor" can include, but is not limited to, retinoic acid and/or cyclopamine, either alone or in combination.

As used herein, "long-term," when used in relation to the survival and functioning of foreign therapeutic cells used in a cell-based therapy/implant, means a period of at least six months or longer.

As used herein, the phrases "therapeutically effective amount" means an amount of encapsulated cells transplanted into a subject that provides the specific pharmacological effect for which the cells are transplanted, i.e. to produce insulin and regulate blood glucose. It is emphasized that a therapeutically effective amount of encapsulated cells will not always be effective in treating diabetes in a given subject, even though such concentration is deemed to be a therapeutically effective amount by those of skill in the art. For convenience only, exemplary amounts are provided below.

Those skilled in the art can adjust such amounts in accordance with standard practices as needed to treat a specific subject. The therapeutically effective amount may vary based on the site of implantation, the age and weight of the subject, and/or the subject's condition, including the severity of the subject's disease, the subject's diet, and/or the subject's overall health.

The terms "treatment" or "treating" as used herein with reference to diabetes refer to one or more of: reducing, ameliorating or eliminating one or more symptoms or co-morbidities of diabetes, such as hyper- and hypo-glycemia, heart disease, renal disease, hepatic disease, retinopathy, neuropathy, non-healing ulcers, periodontal disease; reducing the subject's reliance on exogenous insulin to regulate blood glucose, regulating the subject's blood glucose without the use of exogenous insulin; reducing the subject's percentage of glycosylated hemoglobin, or HbA1C levels; and/or reducing the subject's reliance on other pharmaceutical interventions, such as insulin sensitizers, enhancers of glucose excretion, and other treatment modalities known in the art.

The terms "individual," "subject," and "patient" are used interchangeably herein, and refer to any individual mammal subject, e.g., non-human primate, porcine, bovine, canine, feline, equine, or human.

II. Identification of Cells for Cell-Based Therapy

One limitation of conventional cell-based therapy is that different cells possess different propensities to differentiate into mature cell types. For instance, it has been reported that epigenetic signatures of the starting cell population can persist in reprogrammed cells, a phenomenon called "epigenetic memory." As a result, iPS cells and other reprogrammed cells may preferentially differentiate into cells that belong to the same germ layer from which they were derived. Accordingly, in some embodiments, the stem cells used in the disclosed methods for generating insulin-producing cells may be derived from mature endodermal cells that have been reprogrammed into pluripotent or multipotent stem cells. In some embodiments, the stem cells used in the disclosed methods may be derived from human pancreatic cells that have been reprogrammed. Such donor pancreatic cells may come from the subject being treated for diabetes (i.e., an autologous donor) or from a person that is not being treated for diabetes (i.e., an allogeneic donor). In some embodiments, the stem cells used in the disclosed methods may be reprogrammed primary cells from the islets of Langerhans of consented healthy adult donor pancreata (see, e.g., FIG. 1A).

Primary cells grown in cell culture can become homogenous and lose functional mature traits over time, possibly as a result of adaptation to artificial culture conditions or genetic drift. Accordingly, when primary cells are used as a starting cell population, it may be advantageous to reprogram the primary cells within, for example, 7 days, 6 days, 5 days, 4 days, 3 days, 2 days, or within 1 day of cell harvest or isolation. For examples, isolated primary cells may be transduced with reprogramming genes within 5 days of cell harvest.

Those of ordinary skill in the art will understand that when primary cells are reprogrammed using reprogramming genes, there are numerous combinations of reprogramming genes that can be used. In some embodiments, a primary cell can be reprogrammed via transduction with Oct4, Sox2, Klf4, and L-Myc. In some embodiments, a primary cell can be reprogrammed via transduction with Oct4, Sox2, Klf4, and C-Myc. In some embodiments, a primary cell can be reprogrammed via transduction with LIN28, Oct4, Sox2, and Nanog. In some embodiments, a primary cell can be reprogrammed via transduction with Glisl, Oct-3/4, Sox2, and Klf4. These exemplary combinations are not intended to be limiting, as other combinations of reprogramming genes are known in the art and may be used for purpose of the disclosed methods.

In some embodiments, the cells used in the disclosed differentiation and treatment methods may possess a preference for differentiating toward one germ line over another. For instance, in some embodiments, a primary cell or stem cell (e.g., SR1423) may efficiently differentiate to ectoderm or endoderm lineages, but substantially unable to differentiate into a mesodermal lineage. This could be determined by, for example, employing differentiation protocols or kits to push a stem cell toward a specific germ line, yet failing to detect a germ line marker (e.g., OTX2 for ectoderm, Sox17 for endoderm, or Brachyury for mesoderm).

In some embodiments, a stem cell or primary cell that preferentially differentiates along an endodermal lineage can be identified by certain molecular markers. For example, a stem cell or primary cell that preferentially differentiates along an endodermal lineage may express markers typical of pluripotency (see, e.g., FIG. 3A) and a normal karyotype (see, e.g., FIG. 3B), yet even if markers typical of pluripotency are expressed, the stem cells may be multipotent or totipotent, and therefore not fit the accepted criteria for pluripotency.

A stem cell or primary cell that preferentially differentiates along an endodermal lineage may also possess a unique gene expression profile. For example, in some embodiments, a stem cell or primary cell that preferentially differentiates along an endodermal lineage may down-regulate expression of BHMT2, Cox7A1, and HSPB2 relative to a control level or control cell. In some embodiments, a stem cell or primary cell that preferentially differentiates along an endodermal lineage may up-regulate expression of NAP1L1 relative to a control level or control cell. Additionally, cells that preferentially differentiate along an endodermal lineage may up-regulate expression of GLIS2, CCDC58, and MTX3 and down-regulate expression of C7orf29 relative to a control cell. Expression levels may be determined by any means known in the art, such as qRT-PCR or microarray analysis, and the control cells used as a standard of comparison may include pluripotent cells that do not exhibit preferential differentiation to the endodermal lineage or a substantial inability to differentiate to the mesodermal lineage, such as the standard embryonic stem cell lines found in the NIH registry. While not being bound by theory, it is believed that at least BHMT2 and NAP1L1 play roles in DNA modification and may contribute to epigenetic memory.

In some embodiments, the differential expression of BHMT2, Cox7A1, HSPB2, and/or NAP1L1 may be at least about 1 log, at least about 2 logs, or at least about 3 logs increased (for BHMT2, Cox7A1, and HSPB2) or decreased (for NAP1L1) relative to pluripotent cell that does not display preferential differentiation to the endodermal lineage and is not substantially unable to differentiate to the mesodermal lineage, or a stem cell that meets the standard criteria for pluripotency.

Identifying a stem cell with the disclosed expression profile indicates a preference for differentiating into an endodermal lineage and thereafter an insulin-producing cell. Direct testing of differentiation preference to specific germ layers increases efficiency of generating cell lines inclined to a particular fate and therefore are suitable for cell-based therapy.

III. Protocol for generating insulin producing beta cells

It has been shown that mammalian stem cells (e.g., iPS cells, embryonic stem cells, and reprogrammed cells) can be differentiated into insulin-producing beta cells by mimicking embryonic pancreatic development. See e.g. Borowiak M. et al. Curr Opin Cell Biol., 21:727-32 (2009). Pluripotent cells differentiate into pancreatic cells in stages. The first stage is differentiation towards the endoderm lineage. The endoderm cells are further differentiated into multipotent pancreatic progenitor cells, which can then be differentiated into islet cells, and the islet cells can then be differentiated into beta cells that produce insulin upon glucose exposure. Current differentiation protocols try to mimic these stages in vitro; however, the efficiency and the success of clinical adaptation of these differentiation protocols vary considerably. See e.g. Pagliuca F W, et al. Cell, 154(2):428-439 (2014). Indeed, current differentiation protocols must often be adapted according to the individual cell to which they are applied. This has prevented establishment of a universal, standardized differentiation protocol to date. In fact, some consistent guidance from current differentiation protocols may inhibit the differentiation of a stem cell line from a different genetic background. The improved methods disclosed herein addresses this deficiency in the art. For example, in some embodiments, the disclosed protocols can robustly generate insulin-producing beta cells from a variety of cellular sources, in contrast with other differentiation protocols that may be cell-specific.

Conventional means of generating insulin producing cells comprises culturing and differentiating stem cells. For the disclosed protocols, cell sources may include, but are not limited to, human embryonic stem cells, induced pluripotent stem cells, non-pluripotent reprogrammed cells (e.g., SR1423), and other conventional cell sources known in the art.

The disclosed methods of generating insulin-producing cells from stem cells comprise a multi-step process wherein endoderm differentiation is first initiated, followed by differentiation to the pancreatic lineage, followed by differentiation to the endocrine lineage, and finally, a maturation process to insulin-producing cells. The endoderm differentiation is typically initiated by contacting the stem cells with an endoderm-inducing agent, such as Activin-A or Wortmannin or a combination thereof. When a sufficient number of endoderm cells have been reached, the cells are contacted with an endocrine-inducing agent, such as retinoic acid or cyclopamine or a combination thereof, to further differentiate the cells into pancreatic progenitor cells. Through exposure to further differentiation factors, which are discussed in more detail below, the pancreatic progenitor cells can be matured into insulin-producing cells that can be used for cell-based therapies to treat diabetes.

In some embodiments, stem cells are cultured in a first medium comprising an endoderm-inducing agent. In some embodiments, the endoderm-inducing agent comprises at least Activin-A. In some embodiments, the endoderm-inducing agent comprises Activin-A and Wortmannin. In some embodiments, the disclosed methods do not employ or include use of an activator of Wnt signaling, such as CHIR-99021 (a small molecule activator of Wnt signaling) and/or the growth factor Wnt3A. Exposure of the stem cells to an endoderm-inducing agent results in differentiation of the cells into endoderm cells.

In contrast to conventional methods of obtaining insulin-producing cells, in some embodiments, the disclosed differentiation method does not employ an activator of Wnt signaling. In contrast to conventional methods, in some embodiments, the disclosed differentiation method exposes the cells long-term to retinoic acid (RA). In contrast to conventional methods, in some embodiments, the disclosed differentiation protocol exposes the cell long-term to cyclopamine or a chemical analog. In contrast to conventional methods, in some embodiments, the disclosed differentiation protocol does not employ the creation of three-dimensional suspension cultures through dissociation of adhesion cultures and re-aggregation of cells in suspension.

In some embodiments, the disclosed differentiation method does not expose the stem cells to Keratinocyte Growth Factors (KGF). KFG has long been considered a necessary component to promote differentiation of beta cells from pancreatic progenitors. See e.g. Movassat J., *Diabetologia*, 46:822-829 (2003). KGF has been reported to promote the differentiation of beta-cells in vivo, particularly in fetal pancreatic tissue, where pancreatic duct cells are formed in the presence of KGF and noggin. Accordingly, application of KGF during the early steps of endoderm differentiation in culture was therefore a reasonable assumption in the development of previous protocols. In some embodiments, the disclosed differentiation method may include exposing the stem cells to KGF.

But here, the present inventors unexpectedly found that in order for KGF to be effective, pancreatic progenitors must have been established through retinoic acid (RA) signaling. Indeed, it was determined that treatment with KGF, in the absence of other factors, produced a negative effect on beta-cell differentiation. Likewise, the present disclosure shows that excluding KGF from the early endoderm stages and adding KGF at later pancreatic progenitor stages improves beta cell production from a variety of cellular sources and results in the production of nearly homologous cultures of insulin-producing cells. Thus, in one aspect, the present disclosure provides novel differentiation methods for obtaining insulin-producing cells in which stem cells are not contacted with KGF prior to or concurrently with endoderm-inducing agents. Rather, the cells are only contacted with KGF at later stages of differentiation. For example, KGF may be introduced to the cells at the same time at which the cells are contacted with RA or at later culturing steps, but not before.

Thus, in some embodiments, differentiating cells are only contacted with KGF in the late stages of endoderm differentiation, such as after the cell has been differentiated into an endocrine cell. Prior to this stage, the stem cells should not be contacted with KGF. Accordingly, the medium used to differentiate stem cells into endoderm cells can comprise Activin-A and/or Wortmannin, but it should not include KGF. In some embodiments, the medium used to differentiate stem cells into endoderm cells can comprise Activin-A, Wortmannin, and/or an activator of Wnt signaling, such as CHIR-99021 (a small molecule activator of Wnt signaling) and/or the growth factor Wnt3A, and combinations thereof, but it should not include KGF.

In some embodiments, the step of differentiating stem cells to endoderm cells may comprise culturing the cells for 1-4 days in a medium comprising Activin-A, Wortmannin, and combinations thereof with or without KGF. For example, the stem cells may be cultured in the presence of these endoderm-inducing agents for about 1, about 2, about 3, or about 4 days, thereby differentiating the stem cells into endoderm cells.

In some embodiments, the stem cells are differentiated into endoderm cells in the presence of Activin A at a concentration of about 1 to about 200 ng/mL, about 25 to about 175 ng/mL, about 50 to about 150 ng/mL, or about 75 to about 125 ng/mL. For example, the Activin A concentration may be about 1 ng/mL, about 10 ng/mL, about 20 ng/mL, about 40 ng/mL, about 50 ng/mL, about 60 ng/mL, about 70 ng/mL, about 80 ng/mL, about 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, or about 200 ng/mL.

In some embodiments, the stem cells are differentiated into endoderm cells in the presence of Wortmannin at a concentration of about 0.1 to about 2.0 uM, about 0.25 to about 1.75 uM, about 0.5 to about 1.5 uM, or about 0.75 to about 1.25 uM. For example, the Wortmannin concentration may be about 0.1 uM, about 0.5 uM, about 1.0 uM, about 1.5 uM, or about 2.0 uM.

In some embodiments, the medium used to differentiate endoderm cells to endocrine cells can comprise KGF, but in some embodiment, the medium used to differentiate endoderm cells to endocrine cell can comprise retinoic acid, Noggin, or cyclopamine and combinations thereof without KGF.

In some embodiments, the step of differentiating endoderm cells to endocrine cells may comprise culturing the cells for 1-5 days in a medium comprising retinoic acid, cyclopamine, and/or noggin, with or without KGF. For example, the endoderm cells may be cultured in the presence of these endocrine-inducing agents for about 1, about 2, about 3, about 4, or about 5 days, thereby differentiating the endoderm cells into endocrine cells.

In some embodiments, the cells are differentiated in the presence of retinoic acid for at least twenty (20) days at a concentration of about 0.05 uM, about 0.1 uM, about 0.5 uM, about 1.0 uM, about 1.5 uM, or about 2.0 uM.

In some embodiments, the cells are differentiated in the presence of cylopamine for at least twenty (20) days at a concentration of about 0.05 uM, about 0.1 uM, about 0.25 uM, or about 0.5 uM.

In some embodiments, the cells are differentiated in the presence of a chemical analog of cyclopamine SANT-1 ((4-Benzyl-piperazin-1-yl)-(3,5-dimethyl-1-phenyl-1H-pyrazol-4-ylmethylene)-amine) at a concentration of about 0.05 uM, about 0.1 uM, about 0.25 uM, or about 0.5 uM.

In some embodiments, the endoderm cells are differentiated into endocrine cells in the presence of retinoic acid at a concentration of about 1.0 to about 10.0 uM, about 2.0 to about 8.0 uM, or about 3.0 to about 5.0 uM. For example, the retinoic acid concentration may be about 1.0 uM, about 1.5 uM, about 2.0 uM, about 2.5 uM, about 3.0 uM, about 3.5 uM, about 4.0 uM, about 4.5 uM, about 5.0 uM, about 5.5 uM, about 6.0 uM, about 6.5 uM, about 7.0 uM, about 7.5 uM, about 8.0 uM, about 8.5 uM, about 9.0 uM, about 9.5 uM, or about 10.0 uM.

In some embodiments, the endoderm cells are differentiated into endocrine cells in the presence of cyclopamine at a concentration of about 0.1 to about 1.0 uM or about 0.25 to about 0.75 uM. For example, the cyclopamine concentration may be about 0.1 uM, about 0.2 uM, about 0.25 uM, about 0.3 uM, about 0.4 uM, about 0.45 uM, about 0.5 uM, about 0.55 uM, about 0.6 uM, about 0.7 uM, about 0.75 uM, about 0.8 uM, about 0.9 uM, or about 1.0 uM.

In some embodiments, the endoderm cells are differentiated into endocrine cells in the presence of Noggin at a concentration of about 1 to about 100 ng/mL, about 25 to about 75 ng/mL, or about 60 to about 70 ng/mL. For example, the Noggin concentration may be about 1 ng/mL, about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, or about 100 ng/mL.

In some embodiments, the endoderm cells are differentiated into endocrine cells in the presence of KGF at a concentration of 1 to about 100 ng/mL, about 25 to about 75 ng/mL, or about 60 to about 70 ng/mL. For example, the KGF concentration may be about 1 ng/mL, about 10 ng/mL, about 20 ng/mL, about 40 ng/mL, about 50 ng/mL, about 60 ng/mL, about 70 ng/mL, about 80 ng/mL, about 90 ng/mL, or about 100 ng/mL. In some embodiments, the cells are not exposed to KGF until after the cells have been differentiated from endoderm cells to endocrine cells.

In some embodiments, the endocrine cells can be further cultured in the presence of additional growth factors and/or hormones in order to differentiate the endocrine cells into pancreatic progenitor cells, and then, ultimately, insulin-producing cells. In some embodiments, the endocrine cells may be cultured in a medium comprising KGF after being exposed to endocrine-inducing agents such as retinoic acid and/or cyclopamine, thereby differentiating the endocrine cells into pancreatic progenitor cells. In some embodiments, the endocrine cells may be cultured in a medium comprising KGF, Noggin, and/or Epidermal Growth Factor (EGF) or combinations thereof, after being exposed to endocrine-inducing agents such as retinoic acid and/or cyclopamine.

In some embodiments, the step of differentiating endocrine cells to pancreatic progenitor cells may comprise culturing the cells for 1-5 days in a medium comprising KGF, Noggin, and/or Epidermal Growth Factor (EGF) or combinations thereof. In some embodiments, the step of differentiating endocrine cells to pancreatic progenitor cells may comprise culturing the cells for 1-5 days in a medium comprising KGF, Noggin, and/or Epidermal Growth Factor (EGF) or combinations thereof and further comprising retinoic acid and/or cyclopamine (e.g., cyclopamine KAAD). For example, the endoderm cells may be cultured in the presence of these agents for about 1, about 2, about 3, about 4, or about 5 days, thereby differentiating the endocrine cells into pancreatic progenitor cells.

In some embodiments, the endocrine cells are differentiated into pancreatic progenitor cells in the presence of KGF at a concentration of 1 to about 100 ng/mL, about 25 to about 75 ng/mL, or about 60 to about 70 ng/mL. For example, the KGF concentration may be about 1 ng/mL, about 10 ng/mL, about 20 ng/mL, about 40 ng/mL, about 50 ng/mL, about 60 ng/mL, about 70 ng/mL, about 80 ng/mL, about 90 ng/mL, or about 100 ng/mL.

In some embodiments, the endocrine cells are differentiated into pancreatic progenitor cells in the presence of Noggin at a concentration of about 1 to about 100 ng/mL, about 25 to about 75 ng/mL, or about 60 to about 70 ng/mL. For example, the Noggin concentration may be about 1 ng/mL, about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, or about 100 ng/mL.

In some embodiments, the endocrine cells are differentiated into pancreatic progenitor cells in the presence of EGF at a concentration of about 1 to about 100 ng/mL, about 25 to about 75 ng/mL, or about 60 to about 70 ng/mL. For example, the EGF concentration may be about 1 ng/mL, about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, or about 100 ng/mL.

In some embodiments, the endocrine cells are differentiated into pancreatic progenitor cells in the presence of retinoic acid at a concentration of about 1 to about 200 ng/mL, about 50 to about 200 ng/mL, or about 75 to about 125 ng/mL. For example, the retinoic acid concentration may be about 1 ng/mL, about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, about 100 ng/mL, about 105 ng/mL, about 110 ng/mL, about 115 ng/mL, about 120 ng/mL, about 125 ng/mL, about 130 ng/mL, about 135 ng/mL, about 140 ng/mL, about 145 ng/mL, about 150 ng/mL, about 155 ng/mL, about 160 ng/mL, about 165 ng/mL, about 170 ng/mL, about 175 ng/mL, about 180 ng/mL, about 185 ng/mL, about 190 ng/mL, about 195 ng/mL, or about 200 ng/mL.

some embodiments, the endocrine cells are differentiated into pancreatic progenitor cells in the presence of cyclopamine at a concentration of about 0.1 to about 1.0 uM or about 0.25 to about 0.75 uM. For example, the cyclopamine concentration may be about 0.1 uM, about 0.2 uM, about 0.25 uM, about 0.3 uM, about 0.4 uM, about 0.45 uM, about 0.5 uM, about 0.55 uM, about 0.6 uM, about 0.7 uM, about 0.75 uM, about 0.8 uM, about 0.9 uM, or about 1.0 uM.

In some embodiments, the pancreatic progenitor cells can be further cultured in the presence of additional growth factors and/or hormones in order to differentiate the pancreatic progenitor cells toward a pancreatic lineage, and, ultimately, into insulin-producing cells. In some embodiments, the pancreatic progenitor cells may be cultured in a medium comprising Noggin, EGF, γ-secretase inhibitor XXI, Alk5i II, and/or T3 and combinations thereof. In some embodiments, the pancreatic progenitor cells may be cultured in a medium comprising Noggin, EGF, γ-secretase inhibitor XXI, Alk5i II, and/or T3 and combinations thereof and further comprising retinoic acid and/or cyclopamine (e.g., cyclopamine KAAD). In some embodiments, T3 may not be included in the culture medium at this stage of differentiation. For example, the pancreatic progenitor cells may be cultured in the presence of these agents for about 1, about 2, about 3, about 4, or about 5 days, thereby differentiating the pancreatic progenitor cells into a pancreatic lineage.

In some embodiments, the pancreatic progenitor cells are further cultured in the presence of Noggin at a concentration of about 1 to about 100 ng/mL, about 25 to about 75 ng/mL, or about 60 to about 70 ng/mL. For example, the Noggin concentration may be about 1 ng/mL, about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, or about 100 ng/mL.

In some embodiments, the pancreatic progenitor cells are further cultured in the presence of EGF at a concentration of about 1 to about 100 ng/mL, about 25 to about 75 ng/mL, or about 60 to about 70 ng/mL. For example, the EGF concentration may be about 1 ng/mL, about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, or about 100 ng/mL.

In some embodiments, the pancreatic progenitor cells are further cultured in the presence of γ-secretase inhibitor XXI at a concentration of about 0.1 to about 2.0 uM, about 0.25 to about 1.75 uM, about 0.5 to about 1.5 uM, or about 0.75 to about 1.25 uM. For example, the γ-secretase inhibitor XXI concentration may be about 0.1 uM, about 0.5 uM, about 1.0 uM, about 1.5 uM, or about 2.0 uM.

In some embodiments, the pancreatic progenitor cells are further cultured in the presence of Alk5i II at a concentration of about 1.0 to about 50.0 uM about 5 to about 25 uM, or about 10 to about 20 uM. For example, the Alk5i II concentration may be about 0.1 uM, about 1.0 uM, about 5.0 uM, about 10 uM, about 20 uM, about 30 uM, about 40 uM, or about 50 uM.

In some embodiments, the pancreatic progenitor cells are further cultured in the presence of T3 at a concentration of about 0.1 to about 2.0 uM, about 0.25 to about 1.75 uM, about 0.5 to about 1.5 uM, or about 0.75 to about 1.25 uM. For example, the T3 concentration may be about 0.1 uM, about 0.5 uM, about 1.0 uM, about 1.5 uM, or about 2.0 uM.

In some embodiments, the pancreatic progenitor cells are further cultured in the presence of retinoic acid at a concentration of about 1 to about 200 ng/mL, about 50 to about 200 ng/mL, or about 75 to about 125 ng/mL. For example, the retinoic acid concentration may be about 1 ng/mL, about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, about 100 ng/mL, about 105 ng/mL, about 110 ng/mL, about 115 ng/mL, about 120 ng/mL, about 125 ng/mL, about 130 ng/mL, about 135 ng/mL, about 140 ng/mL, about 145 ng/mL, about 150 ng/mL, about 155 ng/mL, about 160 ng/mL, about 165 ng/mL, about 170 ng/mL, about 175 ng/mL, about 180 ng/mL, about 185 ng/mL, about 190 ng/mL, about 195 ng/mL, or about 200 ng/mL.

some embodiments, the pancreatic progenitor cells are further cultured in the presence of cyclopamine at a concentration of about 0.1 to about 1.0 uM or about 0.25 to about 0.75 uM. For example, the cyclopamine concentration may be about 0.1 uM, about 0.2 uM, about 0.25 uM, about 0.3 uM, about 0.4 uM, about 0.45 uM, about 0.5 uM, about 0.55 uM, about 0.6 uM, about 0.7 uM, about 0.75 uM, about 0.8 uM, about 0.9 uM, or about 1.0 uM.

In some embodiments, the pancreatic cells can be further cultured in the presence of additional growth factors and/or hormones in order to ultimately differentiate the cells into insulin-producing cells. In some embodiments, the pancreatic progenitor cells may be cultured in a medium comprising Alk5i II, T3, and/or retinoic acid and combinations thereof. In some embodiments, the pancreatic progenitor cells may be cultured in a medium comprising Alk5i II, T3, and/or retinoic acid and combinations thereof and further comprising cyclopamine (e.g., cyclopamine KAAD). In some embodiments, T3 may not be included in the culture medium at this stage of differentiation. For example, the pancreatic progenitor cells may be cultured in the presence of these agents for about 1, about 2, about 3, about 4, or about 5 days, thereby differentiating the pancreatic cells toward an insulin-producing cell type.

In some embodiments, the pancreatic cells are further cultured in the presence of Alk5i II at a concentration of about 1.0 to about 50.0 uM about 5 to about 25 uM, or about 10 to about 20 uM. For example, the Alk5i II concentration may be about 0.1 uM, about 1.0 uM, about 5.0 uM, about 10 uM, about 20 uM, about 30 uM, about 40 uM, or about 50 uM.

In some embodiments, the pancreatic cells are further cultured in the presence of T3 at a concentration of about 0.1 to about 2.0 uM, about 0.25 to about 1.75 uM, about 0.5 to about 1.5 uM, or about 0.75 to about 1.25 uM. For example, the T3 concentration may be about 0.1 uM, about 0.5 uM, about 1.0 uM, about 1.5 uM, or about 2.0 uM.

In some embodiments, the pancreatic cells are further cultured in the presence of retinoic acid at a concentration of about 1 to about 200 uM, about 25 to about 175 uM, about 50 to about 150 uM, or about 75 to about 125 uM. For example, the retinoic acid concentration may be about 1 uM, about 10 uM, about 20 uM, about 40 uM, about 50 uM, about 60 uM, about 70 uM, about 80 uM, about 90 uM, about 100 uM, about 110 uM, about 120 uM, about 130 uM, about 140 uM, about 150 uM, about 160 uM, about 170 uM, about 180 uM, about 190 uM, or about 200 uM. In some embodiments, the pancreatic progenitor cells are further cultured in the presence of retinoic acid at a concentration of about 1 to about 200 ng/mL, about 50 to about 200 ng/mL, or about 75 to about 125 ng/mL. For example, the retinoic acid concentration may be about 1 ng/mL, about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, about 100 ng/mL, about 105 ng/mL, about 110 ng/mL, about 115 ng/mL, about 120 ng/mL, about 125 ng/mL, about 130 ng/mL, about 135 ng/mL, about 140 ng/mL, about 145 ng/mL, about 150 ng/mL, about 155 ng/mL, about 160 ng/mL, about 165 ng/mL, about 170 ng/mL, about 175 ng/mL, about 180 ng/mL, about 185 ng/mL, about 190 ng/mL, about 195 ng/mL, or about 200 ng/mL.

some embodiments, the pancreatic progenitor cells are further cultured in the presence of cyclopamine at a concentration of about 0.1 to about 1.0 uM or about 0.25 to about 0.75 uM. For example, the cyclopamine concentration may be about 0.1 uM, about 0.2 uM, about 0.25 uM, about 0.3 uM, about 0.4 uM, about 0.45 uM, about 0.5 uM, about 0.55 uM, about 0.6 uM, about 0.7 uM, about 0.75 uM, about 0.8 uM, about 0.9 uM, or about 1.0 uM.

In some embodiments, the pancreatic cells can be further cultured in the presence of additional growth factors and/or hormones in order to ultimately differentiate the cells into insulin-producing cells. In some embodiments, the pancreatic progenitor cells may be cultured in a medium comprising Alk5i II, T3, nicotinamide, insulin-like growth factor (IGF)-I, and/or BMP4 and combinations thereof. In some embodiments, the pancreatic progenitor cells may be cultured in a medium comprising Alk5i II, T3, nicotinamide, insulin-like growth factor (IGF)-I, and/or BMP4 and combinations thereof and combinations thereof and further comprising retinoic acid and/or cyclopamine (e.g., cyclopamine KAAD). In some embodiments, T3 and/or BMP4 may not be included in the culture medium at this stage of differentiation. For example, the pancreatic progenitor cells may be cultured in the presence of these agents for about 1, about 2, about 3, about 4, about 5, about 6, about 7, about 8, about 9, or about 10 days, thereby differentiating the pancreatic cells into insulin producing cells.

In some embodiments, the pancreatic cells are further cultured in the presence of Alk5i II at a concentration of about 1.0 to about 50.0 uM about 5 to about 25 uM, or about 10 to about 20 uM. For example, the Alk5i II concentration may be about 0.1 uM, about 1.0 uM, about 5.0 uM, about 10 uM, about 20 uM, about 30 uM, about 40 uM, or about 50 uM.

In some embodiments, the pancreatic cells are further cultured in the presence of T3 at a concentration of about 0.1 to about 2.0 uM, about 0.25 to about 1.75 uM, about 0.5 to about 1.5 uM, or about 0.75 to about 1.25 uM. For example, the T3 concentration may be about 0.1 uM, about 0.5 uM, about 1.0 uM, about 1.5 uM, or about 2.0 uM.

In some embodiments, the pancreatic cells are further cultured in the presence of nicotinamide at a concentration of about 1.0 to about 50.0 mM about 5 to about 25 mM, or about 10 to about 20 mM. For example, the nicotinamide concentration may be about 0.1 mM, about 1.0 mM, about 5.0 mM, about 10 mM, about 20 mM, about 30 mM, about 40 mM, or about 50 mM.

In some embodiments, the pancreatic progenitor cells are further cultured in the presence of IGF-I at a concentration of about 1 to about 100 ng/mL, about 25 to about 75 ng/mL, or about 60 to about 70 ng/mL. For example, the IGF-I concentration may be about 1 ng/mL, about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, or about 100 ng/mL.

In some embodiments, the pancreatic cells are further cultured in the presence of BMP4 at a concentration of about 1.0 to about 50.0 ng/mL about 5 to about 25 ng/mL, or about 10 to about 20 ng/mL. For example, the BMP4 concentration may be about 0.1 ng/mL, about 1.0 ng/mL, about 5.0 ng/mL, about 10 ng/mL, about 20 ng/mL, about 30 ng/mL, about 40 ng/mL, or about 50 ng/mL.

In some embodiments, the pancreatic progenitor cells are further cultured in the presence of retinoic acid at a concentration of about 1 to about 200 ng/mL, about 50 to about 200 ng/mL, or about 75 to about 125 ng/mL. For example, the retinoic acid concentration may be about 1 ng/mL, about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, about 100 ng/mL, about 105 ng/mL, about 110 ng/mL, about 115 ng/mL, about 120 ng/mL, about 125 ng/mL, about 130 ng/mL, about 135 ng/mL, about 140 ng/mL, about 145 ng/mL, about 150 ng/mL, about 155 ng/mL, about 160 ng/mL, about 165 ng/mL, about 170 ng/mL, about 175 ng/mL, about 180 ng/mL, about 185 ng/mL, about 190 ng/mL, about 195 ng/mL, or about 200 ng/mL.

some embodiments, the pancreatic progenitor cells are further cultured in the presence of cyclopamine at a concentration of about 0.1 to about 1.0 uM or about 0.25 to about 0.75 uM. For example, the cyclopamine concentration may be about 0.1 uM, about 0.2 uM, about 0.25 uM, about 0.3 uM, about 0.4 uM, about 0.45 uM, about 0.5 uM, about 0.55 uM, about 0.6 uM, about 0.7 uM, about 0.75 uM, about 0.8 uM, about 0.9 uM, or about 1.0 uM.

In some embodiments, the cells are differentiated on an adhesive substrate comprised of vitronectin and/or laminin and/or collagen. In some embodiments, the cells that spontaneously and naturally form three-dimensional structures are collected and transferred to suspension culture.

In some embodiments, the cells are encapsulated within a hydrogel and differentiation may further proceed while the cells are encapsulated within the hydrogel. In these embodiments, the differentiation protocol is the same as for cells that are not encapsulated (i.e., the differentiation protocol may comprise the same reagents and incubation times as the disclosed differentiation methods). That is, even after being encapsulated within a hydrogel, the cells can still be incubated in the disclosed mediums to produce insulin-producing cells. In some embodiments the hydrogel encapsulating the cells may comprise or consist of sodium alginate. In some embodiments the cells are encapsulated within a hydrogel around day 12 of differentiation. For example, the cells may be encapsulated within a hydrogel on day 8, 9, 10, 11, 12, 13, 14, or 15 of differentiation. Accordingly, the cells may be encapsulated in a hydrogel after they have been incubated in a medium comprising noggin and/or EGF (i.e., the "third medium," as disclosed herein). In some embodiments that cells are encapsulated within a hydrogel at a later stage of differentiation around day 14, around day 16, around day 18, around day 20, around day 22, around day 24, around day 26, or around day 28.

In some embodiments, the stem cells used in the disclosed differentiation method are derived from pancreatic primary tissue. In some embodiments, the stem cells used in the disclosed differentiation method are embryonic stem cells. In some embodiments, the stem cells used in the disclosed differentiation method are induced pluripotent stem cells. In some embodiments, the stem cells used in the disclosed differentiation method are non-pluripotent reprogrammed cells. In some embodiments, the stem cells are human stem cells.

For the purposes of the present disclosure, it may be desirable to reprogram cells by expressing reprogramming genes in the cell without incorporating the reprogramming genes into the genome of the cell. Those of ordinary skill in the art will recognize that transduced genes can be expressed in a cell without incorporating those genes into the genome using, for example, episomal expression plasmids. The reprogramming genes may be expressed on at least 1, at least 2, at least 3, or at least 4 or more episomal expression plasmids. As discussed above, multiple reprogramming genes are known in the art and may be used for the purposed of the disclosed methods, but in some embodiments, the reprogramming genes comprise Oct4, Sox2, Klf4, and L-Myc.

In some embodiments, the total culturing time required for differentiating cells from a stem cell into an insulin-producing cell may be about 30 days or less. For instance, the cells may be cultured for about 30 days, about 29 days, about 28 days, about 27 days, about 26 days, about 25 days, or less.

Those of skill in the art will also understand that the overall culturing time in each differentiation step may vary. Accordingly, in some embodiments, the present disclosure provides a method of producing insulin-secreting pancreatic cells, comprising (a) culturing human stem cells in a first medium comprising Activin-A and Wortmannin, wherein the human cells were not exposed to Wnt3a and optionally are not exposed to keratinocyte growth factors (KGF) prior to differentiation into endoderm cells, thereby differentiating the human stem cells into endoderm cells; (b) culturing the endoderm cells from (a) in a second medium comprising retinoic acid and cyclopamine and optionally comprising KGF, thereby differentiating the endoderm cells into endocrine cells; (c) culturing the endocrine cells from (b) in a third medium comprising KGF, thereby differentiating the endocrine cells into pancreatic progenitor cells; (d) culturing the pancreatic progenitor cells from (c) in a fourth medium comprising noggin, EGF, γ-secretase inhibitor XXI, Alk5i II, and T3; (e) culturing the cells from (d) in a fifth medium comprising Alk5i II, T3, and retinoic acid; and (f) culturing in a sixth medium comprising Alk5i II, T3, nicotinamide, insulin-like growth factor (IGF)-I, and BMP4.

In some embodiments, the present disclosure provides a method of producing insulin-secreting pancreatic cells, comprising (a) culturing human stem cells in a first medium comprising Activin-A and Wortmannin, wherein the human cells were not exposed to Wnt3a and optionally are not exposed to keratinocyte growth factors (KGF) prior to differentiation into endoderm cells, thereby differentiating the human stem cells into endoderm cells; (b) culturing the endoderm cells from (a) in a second medium comprising retinoic acid, noggin and cyclopamine and optionally comprising KGF, thereby differentiating the endoderm cells into endocrine cells; (c) culturing the endocrine cells from (b) in a third medium comprising KGF, noggin, retinoic acid, and cyclopamine, thereby differentiating the endocrine cells into pancreatic progenitor cells; (d) culturing the pancreatic progenitor cells from (c) in a fourth medium comprising noggin, EGF, γ-secretase inhibitor XXI, Alk5i II, retinoic acid, and cyclopamine; (e) culturing the cells from (d) in a fifth medium comprising Alk5i II, T3, retinoic acid, and cyclopamine; and (f) culturing in a sixth medium comprising Alk5i II, nicotinamide, IGF-I, retinoic acid, and cyclopamine.

In some embodiments, the sixth medium may comprise glucagon, which has a beneficial effect in reducing the proportion of endocrine cells that co-express insulin and glucagon. The concentration of glucagon may be, for example, about 40 ng/L, about 70 ng/L, about 110 ng/L, or about 140 ng/L.

In some embodiments, the total culturing time for steps (a)-(f) may be 30 days or less. For instance, the cells may be cultured for about 30 days, about 29 days, about 28 days, about 27 days, about 26 days, about 25 days, or less. In some embodiments, step (a) may comprise days 1-3 of culture, step (b) may comprise days 4-7 of culture, step (c) may comprise days 8-11 of culture, step (d) may comprise days 12-15 of culture, step (e) may comprise days 16-19 of culture, and step (f) may comprise days 20-28 of culture. Accordingly, in some embodiments, step (a) may comprise 1-4 days of culturing, step (b) may comprise 1-5 days of culturing, step (c) may comprise 1-5 days of culturing, step (d) may comprise 1-5 days of culturing, step (e) may comprise 1-5 days of culturing, and step (f) may comprise 1-10 days of culturing.

As disclosed herein, exposing differentiating cells to KGF at the earlier endoderm stages may obstruct generation of insulin producing beta cells, and therefore the addition of this component is optional and may vary depending on the precise protocol. For the purposes of preparing insulin-producing cells, in some embodiments it may therefore beneficial to exclude KGF from the early stages of endoderm differentiation or until at least a time in culture in which the differentiating cells have been exposed to retinoic acid.

In some embodiments, the present disclosure provides a method of producing insulin-secreting pancreatic cells, comprising (a) culturing human stem cells in a first medium comprising Activin-A and Wortmannin, wherein the human cells were not exposed to Wnt3a, thereby differentiating the human stem cells into endoderm cells; (b) exposing the cells during subsequent culture steps to retinoic acid for at least twenty (20) days; (c) exposing the cells during subsequent culture steps to cyclopamine or a chemical analog for at least twenty (20) days; (d) initiating cell culture on an adhesive substrate; and (e) transferring cells that naturally and spontaneously form three-dimensional structures to suspension culture; and optionally (f) culturing the cells in the presence of glucagon.

In some embodiments, the present disclosure provides methods of producing mammalian insulin-secreting cells, comprising: culturing mammalian stem cells in adhesion, thereby allowing the mammalian stem cells to spontaneously form three-dimensional structures; and culturing of the three-dimensional structures in suspension; wherein the culturing steps comprise at least a 20-day exposure to retinoic acid and cyclopamine, and do not comprise exposing the stem cells of three-dimensional structures to Wnt3A.

In some embodiments, the present disclosure provides methods of producing insulin-secreting cells, comprising: culturing mammalian stem cells on an adhesive substrate in a first medium comprising Activin-A and Wortmannin, wherein the mammalian stem cells are not exposed to Wnt3a; further culturing the cells in at least one additional medium comprising retinoic acid and cyclopamine; and transferring the cells to a suspension culture when the cells form three-dimensional cell structures; wherein the cells are exposed to retinoic acid and cyclopamine for at least 20 days.

In some embodiments, it may be preferable to select a starting stem cell or non-pluripotent progenitor cell that preferentially differentiates or is predisposed to differentiation to the endoderm lineage. This may allow for simpler differentiation and may achieve a purer and more mature culture of insulin-secreting cells compared to traditional methods.

For the purposes of the presently disclosed method, it was determined that the production of insulin-secreting cells is optimized when the cells are initially grown in adhesion or the culture is initiated on an adhesive substrate (e.g., a positively charged surface or a surface coated with vitronectin or Matrigel), thus allowing the cells to naturally and spontaneously form three-dimensional structures (e.g., aggregates of cells). These three-dimensional structures made up of adhered cells can then be cultured in suspension for the duration of the disclosed methods.

Thus, in some embodiments, the starting stem cell population is grown in adhesion, while the later stages of culture take place in suspension. For the purposes of this disclosure, the phrases "grown in adhesion" or "cultured in adhesion" refer to standard cell culture wherein cells adhere to the surface of the culture dish. In some cases, the culture dish may be coated with a substrate to promote adhesion, and in some cases the dish may be given a net positive charge to promote adhesion. In general, culturing of stem cells, such as iPS cells, requires an adhesive substrate, and various adhesion-promoting substrates are known in the art. For example, one vitronectin or Matrigel can be applied to a cell flask to promote adhesion, but Matrigel is harvested from mouse sarcoma cells and is therefore not preferred for clinical use. In some embodiments, differentiation is commenced by culturing the starting stem cell population with an endoderm-inducing media, and grown in adhesion. Formation of 3D structures (e.g., aggregates of differentiated/differentiating cells) on the substrate/plate may occur gradually as differentiation progresses. By day about 15, the 3D structures begin to detach from the plate, and these 3D structures can be transferred into vessels that are not coated with an adhesive substrate (e.g., vitronectin), such that the 3D structures are cultured in a free-floating suspension. This transition, from culturing in adhesion to a suspension culture is novel and allows for a more natural differentiation into an insulin-secreting cell.

It was also determined that, contrary to conventional practice, the stem cells used to initiate the culture do not need to be contacted with Wnt3a in order to facilitate differentiation. Indeed, Wnt3a is not required at any point in the disclosed methods.

Lastly, it was determined that even as various differentiation mediums are exchanged throughout the process of producing insulin-secreting cells, differentiation appears to be most efficient when the cells remain in contact with at least some concentration of retinoic acid and cyclopamine for at least about 20 days. For example, in some embodiments, the cells are preferably exposed to retinoic acid and cyclopamine for at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, or at least about 28 days. In some embodiments, this continued exposure to retinoic acid and cyclopamine may commence after the starting stem cell population has been forced toward an endodermal lineage, for example, after the starting stem cell population has been cultured in the presence of Activin A and wortmannin for about 1, about 2, about 3, about 4, or about 5 days.

Those of skill in the art will understand that the disclosed methods can be applied generally to mammalian stem cells, such as human and non-human primate stem cells. However, additional mammalian cells, such as pig, cow, horse, sheep, dog, or cat stem cells may also be differentiated according to the disclosed methods. Additionally, those of skill in the art will recognize that the disclosed methods can employ various forms of cells culture including, for example, adherent cultures and/or suspension cultures.

The disclosed protocols for generating insulin-producing cells enhanced the yield of insulin-producing beta cells from both human embryonic stem cells and reprogrammed pancreatic tissue. In contrast to conventional methods of producing insulin producing cells, the protocol disclosed herein yields near homogeneous populations of insulin-producing cells. Producing a homologous cell population is not only important for therapeutic efficacy, but also for safety, as stems cells can form teratomas when transplanted and have tumorigenic potential. The high degree of differentiation and homogeneity provided by the disclosed differentiation methods means fewer cells with tumorigenic potential, which is essential in the development of a useful cell therapy.

Prior to employing the disclosed differentiation methods, stem cells that preferentially differentiate into endoderm cell may be identified according to the methods disclosed in Section II of this application. This can increase the overall efficiency of the differentiation process as well as increase the yield of insulin-producing cells.

IV. Cell-Based Compositions and Methods of Treatment

The insulin-producing cells disclosed herein can be used to treat diabetes in a subject in need thereof. In some embodiments, the subject in need of treatment is a mammal, for example, a human subject with insulin-dependent diabetes.

The present disclosure provides methods for producing a population of substantially homologous insulin-producing cells, which can be incorporated into a cell-based composition for treating diabetes. Accordingly, provided herein are cell-based compositions for treating diabetes, comprising a population of surrogate pancreatic cells and a suitable carrier for implantation into a human subject in need thereof, wherein at least 66% of the cells are insulin-producing pancreatic cells. In some embodiments, the cell-based composition may comprise at least about 67%, at least about 68%, at least about 69%, at least about 70%, at least about 75%, at least about 80%, at least about 85%, at least about 90%, at least about 95%, at least about 96%, at least about 97%, at least about 98%, at least about 99%, or at least about 100% insulin-producing pancreatic cells.

Suitable carriers for implanting therapeutic cells are known in the art and may include but are not limited to hydrogels, natural and synthetic polymer scaffolds, extracellular matrix (which may comprise, e.g., collagen, laminin, fibronectin, etc.), hyaluronic acid, biomimetic scaffolds, polylactide (PLA) scaffolds, polyglycolide (PGA) scaffolds, PLA-PGA copolymer (PLGA) scaffolds, as well as hydroxyapatite scaffolds, and macro-porous cryogels. In some embodiments, the carrier suitable for transplantation may comprise encapsulating the insulin-producing cells in macro-capsules, such as macro-capsules comprising alginate, cellulose sulfate, glucomannan, or a combination thereof.

In some embodiments, at least 66% of the surrogate pancreatic cells express NeuroD1. In some embodiments, at least about 67%, at least about 68%, at least about 69%, at least about 70%, at least about 75%, at least about 80%, at least about 85%, at least about 90%, at least about 95%, at least about 96%, at least about 97%, at least about 98%, at least about 99%, or at least about 100% of the surrogate pancreatic cells express NeuroD1.

In some embodiments, at least 68% of the surrogate pancreatic cells express Nkx6.1 . In some embodiments, at least about 67%, at least about 68%, at least about 69%, at least about 70%, at least about 75%, at least about 80%, at least about 85%, at least about 90%, at least about 95%, at least about 96%, at least about 97%, at least about 98%, at least about 99%, or at least about 100% of the surrogate pancreatic cells express Nkx6.1.

The cell-based compositions for treating diabetes may be prepared according to the methods disclosed herein. For example, the insulin-producing pancreatic cells of a cell-based composition may, for example, be derived according to a method comprising: (a) culturing a population of human stem cells in a first medium comprising an endoderm-inducing factor, thereby differentiating the human stem cells into endoderm cells, wherein the human stem cells were not exposed to keratinocyte growth factors (KGF) prior to differentiation into endoderm cells; (b) culturing the endoderm cells from (a) in a second medium comprising a endocrine-inducing factor, thereby differentiating the endoderm cells into endocrine cells; (c) culturing the endocrine cells from (b) in a third medium comprising KGF, thereby differentiating the endocrine cells into pancreatic progenitor cells; and (d) culturing the pancreatic progenitor cells from (c) in a fourth medium comprising a thyroid hormone, thereby differentiating the pancreatic progenitor cells into insulin-producing pancreatic cells.

In some embodiments, the insulin-producing pancreatic cells of a cell-based composition may, for example, be derived according to a method comprising: (a) culturing a population of human stem cells in a first medium comprising an endoderm-inducing factor, thereby differentiating the human stem cells into endoderm cells, wherein the human stem cells were not exposed to Wnt3a; (b) exposing the cells during subsequent culture steps to retinoic acid for at least twenty (20) days; (c) exposing the cells during subsequent culture steps to cyclopamine or a chemical analog for at least twenty (20) day; (d) initiating cell culture on an adhesive substrate, and; (e) transferring cells that naturally and spontaneously form three-dimensional structures to suspension culture.

In some embodiments, the insulin-producing pancreatic cells of a cell-based composition may, for example, be derived according to a method comprising: culturing a population of human stem cells on an adhesive substrate in a first medium comprising an endoderm-inducing factor, wherein the mammalian stem cells are not exposed to Wnt3a; and further culturing the cells in suspension in at least one additional medium comprising retinoic acid and cyclopamine, wherein the cells are exposed to retinoic acid and cyclopamine for at least 20 days. In some embodiments, the endoderm-inducing factor comprises Activin-A and/or Wortmannin. In some embodiments, the at least one additional medium may comprise KGF, noggin, EGF, and/or a thyroid hormone, such as T3.

Various endoderm-inducing factors are known in the art, including, but not limited to, Activin-A and Wortmannin. Likewise, various endocrine-inducing factor are known in the art, including, but not limited to, retinoic acid and cyclopamine.

In some embodiments, the second medium comprises KGF, while in some embodiments, the cells are not contacted with KGF until after step (b). In some embodiments, KGF may be included in the medium of step (a).

In some embodiments, the third medium comprises noggin and/or epidermal growth factor (EGF). In some embodiments, the third medium comprises retinoic acid and/or cyclopamine. And in some embodiments, the thyroid hormone may be T3.

The source of the stem cells used for preparing the disclosed cell-based composition is not particularly limited; however, choosing a cell/cell line that preferentially differentiates into an endodermal lineage, as disclosed herein, may increase the yield of insulin-producing cells and increase differentiation efficiency. Thus, in some embodiments, the stem cells used in the disclosed differentiation methods for preparing a cell-based composition are derived from pancreatic primary tissue. In some embodiments, the stem cells used in the disclosed differentiation method are embryonic stem cells. In some embodiments, the stem cells used in the disclosed differentiation method are induced pluripotent stem cells. In some embodiments, the stem cells used in the disclosed differentiation method are non-pluripotent reprogrammed cells. In some embodiments, the stem cells are human stem cells.

For the purposes of the present disclosure, when preparing insulin-producing cells for incorporation into a cell-based composition for treating diabetes, it may be desirable to reprogram cells by expressing reprogramming genes in the cell without incorporating the reprogramming genes into the genome of the cell. Those of ordinary skill in the art will recognize that transduced genes can be expressed in a cell without incorporating those genes into the genome using, for example, episomal expression plasmids. The reprogramming genes may be expressed on at least 1, at least 2, at least 3, or at least 4 or more episomal expression plasmids. As discussed above, multiple reprogramming genes are known in the art and may be used for the purposed of the disclosed methods, but in some embodiments, the reprogramming genes comprise Oct4, Sox2, Klf4, and L-Myc.

In some embodiments, the cell-based composition is encapsulated in, for example, micro-capsules or macro-capsules.

The present disclosure also provides methods of treating diabetes using the disclosed cell-based compositions. The methods of treating diabetes generally comprise implanting a therapeutically effective amount of insulin-producing cells encapsulated into a subject in need thereof. The therapeutically effective amount of insulin-producing cells may be in the form of a cell-based composition, for instance, a population of surrogate pancreatic cells that are micro-encapsulated or macro-encapsulated.

Thus, in some embodiments, the methods comprise implanting into an individual in need thereof a therapeutically effective amount of insulin-producing cells encapsulated in macro-capsules. The composition of the macro-capsules is not particularly limited and those of skill in the art will understand that various materials can be used to encapsulate insulin-producing cells. For example, the capsules may comprise alginate, cellulose sulfate, glucomannan, or a combination thereof. In some embodiments, the macro-capsules may comprise at least one barrier in which the outer barrier is comprised of cellulose sulfate and glucomannan. In some embodiments, the macro-capsules may be formed in the shape of a cylindrical tube comprised of an inner capsule of alginate and an outer capsule of cellulose sulfate and glucomannan.

In some embodiments, the methods comprise implanting into an individual in need thereof a therapeutically effective amount of insulin-producing cells encapsulated in the disclosed macro-capsules about once a year, once every two years, once every three years, once every four years, once every five years, or more. In some embodiments, the implanted cells will survive for at least six months after implantation. Accordingly, in some embodiments, the subject may require only one implant. In some embodiments, the cell-based composition may need to be replaced once every 6, 7, 8, 9, 10, 11, 12, 13, 14, 15, 16, 17, or 18 or months, once every 1, 2, 3, 4, or 5 or more years or until the subject has recurring hyperglycemia, or a return to the diabetic state.

In some embodiments, the cell-based composition can be implanted into the greater omentum of the subject. The greater omentum (also known as the great omentum, omentum majus, gastrocolic omentum, epiploon, or, caul) is a large apron-like fold of visceral peritoneum that hangs down from the stomach and extends from the greater curvature of the stomach back to ascend to the transverse colon before reaching to the posterior abdominal wall. Thus, the cell-based composition may be implanted into a pouch formed surgically from the omentum.

In some embodiments, the cell-based composition is implanted into the peritoneal cavity. In some embodiments, cell-based composition is implanted into the peritoneal cavity and anchored to the omentum. In some embodiments, the cell-based composition is implanted into an omentum pouch.

Exemplary doses of insulin-producing cells can vary according to the size and health of the individual being treated. For example, in some embodiments, an exemplary implant of cells encapsulated in the disclosed cell-based composition may comprise 5 million cells to 10 million cells per Kg of body weight.

Furthermore, the disclosed methods of treatment can additionally comprise the administration of a second therapeutic in addition to the encapsulated therapeutic cells. For example, in some embodiments, the additional therapeutic compound can include, but is not limited to, insulin injections, metformin, sulfonylureas, meglitinides, thiazolidinediones, DPP-4 inhibitors, GLP-1 receptor agonists, and SGLT2 inhibitors.

Particular treatment regimens comprising implanting the cell-based composition comprising insulin-producing cells may be evaluated according to whether they will improve a given patient's outcome, meaning it will help stabilize or normalize the subject's blood glucose levels or reduce the risk or occurrence of symptoms or co-morbidities associated with diabetes, including but not limited to, episodes of hypoglycemia, elevated levels of glycosylated hemoglobin (HbA1C levels), heart disease, retinopathy, neuropathy, renal disease, hepatic disease, periodontal disease, and non-healing ulcers. In some embodiments, the cell-based composition will be encapsulated, for example, in a capsule comprising alginate, cellulose sulfate, glucomannan, or a combination thereof.

Thus, for the purposes of this disclosure, a subject is treated if one or more beneficial or desired results, including desirable clinical results, are obtained. For example, beneficial or desired clinical results include, but are not limited to, one or more of the following: decreasing one or more symptoms resulting from diabetes, increasing the quality of life of those suffering from diabetes, decreasing the dose of other medications required to treat diabetes, delaying or preventing complications associated with diabetes, and/or prolonging survival of individuals.

Furthermore, while the subject of the methods is generally a subject with diabetes, the age of the patient is not limited. The disclosed methods are useful for treating diabetes across all age groups and cohorts. Thus, in some embodiments, the subject may be a pediatric subject, while in other embodiments, the subject may be an adult subject.

One skilled in the art will readily appreciate that the present disclosure is well adapted to carry out the objects and obtain the ends and advantages mentioned, as well as those inherent therein. Modifications therein and other uses will occur to those skilled in the art. These modifications are encompassed within the spirit of the disclosure. The following examples are given to illustrate the present invention. It should be understood, however, that the invention is not limited to the specific conditions or details of these examples.

EXAMPLES

Example 1

Materials and Methods

Islet harvest: Properly consented and anonymized whole human pancreata were obtained from registered organ donation. The lobes were injected with collagenase P (Roche #1129 002 001) re-suspended to 1.4 mg/ml in islet isolation solution (Hanks Balanced Salt Solution (Invitrogen #14065-056) containing 0.35 g NaHCO3/L and 1% Human Serum Albumin (Roche A9731)). The inflated lobes were incubated at 37C for 15-25 minutes with mild agitation. The digest was diluted with cold islet isolation solution and centrifuged at 1500 RPM for 5 minutes. The supernatant was discarded and the pellet was washed in cold islet isolation solution with vigorous trituration. The solution was filtered through a 420 µm sieve (Bellco Glass, Inc, Cat# 1985-00040) and centrifuged. The pellet was resuspended in 1.100 g/ml Histopaque (Sigma #10771, Sigma #11191) and centrifuged for 30 min at 1200 RPM. The supernatant was collected, diluted 2× in islet isolation solution and centrifuged at 1500 RPM for 5 min. The pellet was rinsed in islet isolation solution, centrifuged, and cultured in E8 medium (Gibco #A1517001) in a humidified incubator at 37C and 5% $CO_2$. The following day, the islets were centrifuged at 1500 RPM for 5 minutes and re-suspended in undiluted Tryp1E Select 10× (Life Technologies #A12177) and incubated for 10 minutes at 37C. The dissociated islets were diluted in E8 media, centrifuged, re-suspended in E8 supplemented with 100 ng/ml hydrocortisone (Sigma #H0135), 1U/ml thrombin (Sigma #T9326), and 100 ng/ml EGF (Sigma E5036). Cells were cultured on dishes coated with vitronectin (Life Technologies # A14700) following manufacturer's instructions.

Reprogramming: Cells were rinsed with PBS (Gibco #14190144) and incubated in TryplE select 1× for 5 minutes at 37C. Digestion was arrested with E8 medium and cells centrifuged at 1000 RPM for 5 minutes. Cells were re-suspended in BTX electroporation solution (VWR #89130-542) at 2E6 cells/200 ul and added to electroporation cuvette with 20 ug of reprogramming plasmids. 2 reprogramming plasmids comprising EBNA episomal expression sequences, ampicillin resistance, and the reprogramming genes Oct4, Sox2, Klf4, and L-Myc under the control of the CMV promoter were constructed in-house. Electroporation cuvette was pulsed using a gene pulser XL (Bio-Rad). Cells were transferred to vitronectin-coated dishes in E6 medium (Life Technologies # a516401) supplemented with 100ng/ml bFGF (Life Technologies # PHG6015) and 1 uM hydrocortisone. Cells were cultured at 37C in a humidified incubator with 5% $CO_2$. After 24 hours, media was changed with E6 supplemented with 100 ng/ml bFGF, and 1 uM hydrocortisone, and 100 uM sodium butyrate (Sigma # P1269), and changed every other day. Stem cell colonies were manually detached and transferred to vitronectin-coated dishes in E8 medium. 73 lines generated from the primary tissue of two donors were initially screened for the ability to express endodermal markers after 4 days exposure to endoderm-inducing agents Activin-A and Wortmannin. Cultures with the highest proportion of cells expressing endodermal markers were selected. Twenty-four cell lines having passed the first screen were subsequently screened for the ability to express pancreatic markers after exposure to a 12-day pancreatic differentiation protocol. The cell line that consistently generated the highest proportion of pancreatic cells was named SR1423, was banked and used for all subsequent experiments.

Cell line characterization: SR1423 expressed markers typical of pluripotent cells (FIG. 3A) and had a normal karyotype (FIG. 3B). The DNA STR profile of SR1423 confirmed that it is a single cell line that matches the donor tissue (FIG. 3C). Additionally, SR1423 grows at a rate typical of pluripotent cell lines (FIG. 3D). It was observed that other induced pluripotent stem cell (hereinafter called "iPSC) lines from the same donor and reprogramming experiment demonstrated preferential differentiation as well. The iPSC line "B" also differentiated well to endoderm while lines "C" and "D" showed no preference for differentiation to the endodermal lineage (data not shown). In order to determine whether there was a correlation between gene expression profiles and the inability of iPSC to differentiate into specific lineages, whole-genome microarray profiling of expressed genes of SR1423 as well as lines B, C, and D were performed. See e.g. Koyanagi-Aoi M. et al. Proc. Natl. Acad. Sci. 110 (2013). Unsupervised hierarchical clustering analysis based on fold change expression of at least Log2, revealed that SR1423 clustered together with cell line B, but not with from C and D. This identified a gene expression pattern that correlates with robust and preferential differentiation to the endodermal lineage (FIG. 4A). Of the 10 most differentially expressed genes, BHMT2, Cox7A1, HSPB2, and NAP1L1 correlated significantly with ability to form endoderm using a qRT-PCR measure (FIG. 4B).

Stem cell culture: Undifferentiated iPS cells were maintained in 6-well tissue culture plates (Greiner Bio-One #657160) coated with vitronectin XF (Stem Cell Technologies #07180) or 17 ug/cm$^2$ Geltrex (Life Technologies #A1413301) following manufacturer's instructions and fed daily with E8 medium. Cultures were passaged at 75-85% confluence every 3-5 days with 0.5 mM EDTA (Life Technologies #15575) and seeded at 7×10$^3$ cells/cm$^2$.

Differentiation: A first batch of SR1423 cells were seeded at 2.3×10$^4$ cells/cm$^2$ and allowed to grow for 18-24 hours. Cells were then washed with dPBS ($-Mg^{2+}/-Ca^{2+}$) and medium was changed following a 28 day schedule comprised of 6 media formulation as follows: Days 1, 2, 3: DMEM/F-12 medium (Life Technologies #10565018), 0.2% HSA, 1XB27 supplement (Life Technologies #A1486701), 100 ng/ml Activin A and 1 uM Wortmannin; Days 4, 5, 6, 7: DMEM (Life Technologies #10567014), 0.2% HSA, 1XB27 supplement, 4 uM Retinoic Acid, 50 ng/ml KGF, 50 ng/ml Noggin, 0.25 uM Cyclopamine KAAD; Days 8, 10: DMEM, 0.2% HSA, 1XB27 supplement, 50 ng/ml KGF, 50 ng/ml Noggin, 50 ng/ml EGF; Days 12, 14: DMEM, 0.2% HSA, 1XB27 supplement, 50 ng/ml Noggin, 50 ng/ml EGF, 1 uM γ-secretase inhibitor XXI, 10 uM Alk5i II, 1 uM T3; Days 16, 18: DMEM, 0.2% HSA, 1XB27 supplement, 10 uM Alk5i II, 1 uM T3, 100 nM Retinoic Acid; Days 20, 22, 24, 26, 28: CMRL (Life Technologies #11530037), 0.2% HSA, 1× B27 supplement, 1× glutamax (Life Technologies # 35050061), 10 uM Alk5i II, 1 uM T3, 10 mM Nicotinamide, 50 ng/ml IGF-I, 10 ng/ml BMP4. For differentiations with the addition of a second stage employing KGF, medium on days 4, 5, 6 with DMEM, 0.2% BSA, 1XB27 supplement, and 50 ng/ml KGF was inserted into the schedule shifting the remaining stages three days later. The protocol of this embodiment generated highly pure populations of endocrine pancreatic cells by day 28 of differentiation (FIG. 5A). Quantification of representative images revealed populations comprised of cells in which 68% were expressing the endocrine pancreatic marker Nkx6.1 (FIG. 5A, quantified in 5E), 66.8% were expressing the late-stage pancreatic marker NeuroD1 (FIG. 5B, quantified in 5E), and 66.5% were expressing Insulin (FIG. 5D, quantified in 5E). This approach of excluding KGF from the differentiating endoderm cells improved the yield of both pancreas derived stem cells and established human embryonic stem cells. FIG. 6.

A second batch of SR1423 cells were seeded at 6.3×10$^4$ as described above and allowed to grow for 18-24 hours. Cells were then washed with dPBS ($-Mg^{2+}/-Ca^{2+}$) and medium was changed following a 28 day schedule comprised of 6 media formulation as follows: Days 1, 2, 3: DMEM/F-12 medium (Life Technologies #10565018), 0.2% HSA, 1XB27 supplement (Life Technologies #A1486701), 100 ng/ml Activin A (PeproTech #AF-120-14E) and 1 Wortmannin (Sigma #W3144); Days 4, 5, 6, 7: DMEM (Life Technologies #10567014), 0.2% HSA, 1XB27 supplement, 2 μM Retinoic Acid (Sigma #R2625), 50 ng/ml KGF (PeproTech #AF-100-19), 50 ng/ml Noggin (PeproTech #120-10C), 0.25 μM Cyclopamine KAAD (Millipore #239804); Days 8, 10: DMEM, 0.2% HSA, 1XB27 supplement, 50 ng/ml KGF, 50 ng/ml Noggin, 50 ng/ml EGF (PeproTech #AF-100-15), 100 nM Retinoic Acid (Sigma #R2625), 0.25 μM Cyclopamine KAAD (Millipore #239804); Days 12, 14: DMEM, 0.2% HSA, 1XB27 supplement, 50 ng/ml Noggin, 50 ng/ml EGF, 1 μM γ-secretase inhibitor XXI (Millipore #565790), 10 μM AlkSi II (Axxora, #ALX-270-445), 100 nM Retinoic Acid (Sigma #R2625), 0.25 μM Cyclopamine KAAD (Millipore #239804); Days 16, 18: DMEM, 0.2% HSA, 1XB27 supplement, 10 μM AlkSi II, 100 nM Retinoic Acid, 0.25 μM Cyclopamine KAAD (Millipore #239804); Days 20, 22, 24, 26, 28: CMRL (Life Technologies #11530037), 0.2% HSA, 1× B27 supplement, 1× glutamax (Life Technologies # 35050061), 10 μM AlkSi II, 10 mM Nicotinamide (Sigma #N0636), 50 ng/ml IGF-I (PeproTech #100-11), 100 nM Retinoic Acid (Sigma #R2625), 0.25 μM Cyclopamine KAAD (Millipore #239804)), and Glucagon (Sigma #G2044).

Figure 7:
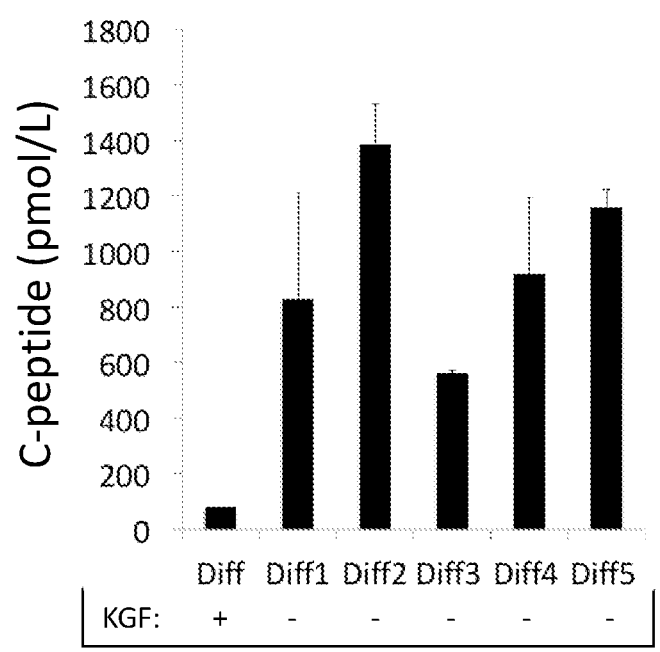
FIG. 7 shows SR1423 differentiation yields cultures with high levels of hormone-secretion. This was established by comparing insulin and glucagon secretion from SR1423 cells and HDC57 cells in response to glucose. Insulin and glucagon levels were assessed via C-peptide (as a proxy for insulin) or glucagon ELISA.

Testing Glucose Stimulated Insulin Secretion: Cells were cultured in CMRL, 0.2% HSA, 1× B27 supplement, 1× glutamax (Life Technologies # 35050061) with 1 g/dL glucose, 10 uM Alk5i II+1 uM T3+10 mM Nicotinamide+50 ng/ml IGF-I+10 ng/ml BMP4 for two hours prior to exposure to glucose solutions. Cells were incubated in 2 mM glucose in KREBS (Alfa Aesar # J67591-AP) for 30 minutes and supernatant collected. Buffer was changed for 20 mM glucose in KREBS for 30 minutes and supernatant collected. Buffer was changed for 20 mM glucose, 30 mM KC1 in KREBS for 30 minutes and supernatant collected. The concentration of C-peptide in each supernatant was determined using an Ultrasensitive C-peptide or Glucagon ELISA (Mercodia #10-1141-01) and a GENios microplate reader (TECAN). Absorbance readings were measured in duplicate using Magellan software (TECAN). Following this procedure, it was observed that cells differentiated from SR1423 secrete insulin using C-peptide as a proxy for insulin (FIG. 7) and glucagon (not shown).

Example 2

Results

Cell line derivation. iPSC lines were generated by introducing reprogramming genes into the nuclei of mature cells. These genes, typically OCT4, Sox2, KLF4, and c-Myc induced a subset of cells to adopt the gene expression pattern, morphology and behavior of embryonic stem cells. It has been reported that epigenetic signatures of the starting cell population persist in the reprogrammed cells, a phenomenon called "epigenetic memory," although the duration of this effect is unknown. To maximize the potential of generating an iPSC line that efficiently differentiates to the pancreatic lineage, primary cells from the islets of Langerhans of consented healthy adult donor pancreata (FIG. 1A) were chosen for reprogramming.

Primary cells grown in cell culture can become homogenous and lose functional mature traits over time, possibly as a result of adaptation to artificial culture conditions. To avoid the loss of genetic diversity in the starting cell population, reprogramming genes were within five days of cell harvest. The reprogramming genes Oct4, Sox2, Klf4, and L-Myc were introduced to the primary cells via electroporation of two episomal expression plasmids. L-Myc was selected over C-Myc to reduce the potential of introducing an oncogenic gene. 73 lines generated from the primary tissue of two donors were initially screened for the ability to express endodermal markers after 4 days exposure to endoderm-inducing agents Activin-A and Wortmannin. Cultures with the highest proportion of cells expressing endodermal markers were selected. Twenty-four cell lines having passed the first screen were subsequently screened for the ability to express pancreatic markers after exposure to a 12-day pancreatic differentiation protocol. The cell line that consistently generated the highest proportion of pancreatic cells was named SR1423, was banked and used for all subsequent experiments. This cell line generated nearly homogenous cultures of definitive endodermal (FIG. 1B), and pancreatic progenitor cells (FIG. 1C). Notably, SR1423 showed robust ability to differentiate in to ectoderm and endoderm (as indicated by OTX2 and Sox17, respectively) but failed to express the mesodermal marker Brachyury when differentiated using a commercial kit (FIG. 2). As all three germ layers were not attained, SR1423 does not fit the accepted criteria of pluripotency for iPSCs and instead may be considered multipotent or non-pluripotent.

Cell line characterization. SR1423 expresses markers typical of pluripotent cells (FIG. 3A) and has a normal karyotype (FIG. 3B). Its DNA STR profile confirms a single cell line that matches the donor tissue (FIG. 3C), and which is unique from all fingerprints in NIH, ATCC, and DSMZ databases. Additionally, SR1423 grows at a rate typical of pluripotent cell lines (FIG. 3D). It was observed that other iPSC cell lines from the same donor and reprogramming experiment demonstrated preferential differentiation as well. The iPSC line "B" also differentiated well to endoderm while iPSC lines "C" and "D" showed no preference for differentiation to the endodermal lineage (data not shown). Whole-genome microarray profiling of expressed genes was performed on SR1423 as well as lines B, C, and D. By this comparison, differences in gene expression due to donor or methods of reprogramming were eliminated. Unsupervised hierarchical clustering analysis based on fold change expression of at least Log2, reveals that SR1423 clusters together with cell line B, but differently from C and D. This identifies a gene expression pattern that correlates with robust and preferential differentiation to the endodermal lineage (FIG. 4A). Of the 10 most differentially expressed genes, BHMT2, Cox7A1, HSPB2, and NAP1L1 correlated significantly with ability to form endoderm using a qRT-PCR measure (FIG. 4B). These results suggest that gene expression of a defined subset of genes could be used to identify a specific iPSC line with therapeutic utility.

Cell differentiation. Other groups reporting production of pancreatic cells from a pluripotent stem cell population use unique cell culture protocols in combination with a unique stem cell population. This means that each protocol was tailored for a particular starting cell population, lending credence to the concept that the starting cell population is a main determinant of differentiation potential.

In most methods, generation of beta cells occurs by the progressive differentiation of the pluripotent cells through the known stages of embryonic pancreatic development. This progression begins with formation of definitive endoderm, followed by transition to pancreatic progenitor, endocrine-committed pancreas, and finally, hormone-expressing pancreatic cells. Conventionally, production of definitive endoderm cells expressing Sox17 and HNF3beta was accomplished by exposure to Activin A and Wnt3a, signaling molecules involved in endodermal patterning in mammals. Pancreatic progenitors, identified by expression of pancreatic duodenal homeobox-1 (Pdx1), arise after activation of HOX genes with retinoic acid, while inhibiting hedgehog signaling with cyclopamine. Endocrine cells expressing both Pdx1 and Nkx6.1 are formed from pancreatic progenitors by activation of KGF signaling, involved in the formation of pancreatic duct cells, in the presence of the patterning protein noggin. Maturation to the hormone expressing phenotype is encouraged by thyroid hormone. Significant effort has been made to replace growth factors and hormones employed in differentiation protocols with small molecules.

The disclosed methods are capable of driving the differentiation of SR1423 and other stem cells into the beta cell phenotype. The disclosed protocol generated highly pure populations of endocrine pancreatic cells by day 28 of differentiation (FIG. 5A). Quantification of representative images revealed populations comprised of cells in which 68% were expressing the endocrine pancreatic marker Nkx6.1, 66.8% were expressing the late-stage pancreatic marker NeuroD1, and 66.5% were expressing Insulin (FIG. 5B).

The present protocol does not provide exposure of the definitive endoderm cells to Wnt3A and optionally does not expose the definitive endoderm to KGF (FGF7), with or without inhibition of TGFβ RI kinase inhibition at days 4-7 of culture. The impact of KGF at earlier stages of differentiation was examined and showed a marked reduction in the production of pancreatic and insulin-producing cells (FIG. 6A). To determine if this result was specific to SR1423 cell lines, the disclosed protocol was compared against known protocols using a reference embryonic stem cell line BGO1V with matching results (FIG. 6B, quantified in 6C). Used side-by-side, the disclosed protocols generated more insulin-producing cells across these cell lines.

Cells differentiated from SR1423 following the disclosed protocol secrete insulin (FIG. 7) and glucagon (not shown) into the media. Sequential differentiations of SR1423 show consistent, reproducibly high levels of C-Peptide detection (FIG. 7) and at greater levels when differentiated with our protocol. These cells can secrete insulin in a glucose-responsive manner (not shown). Consequently, these hormone-secreting cells may be ideal candidates for cell replacement therapies. Furthermore, it is possible to achieve an optimal balance of mature insulin and glucagon-expressing cells by adding glucagon to the culture media, which has the benefit of reducing the amount of cells that co-express insulin and glucagon (FIG. 10A-C).

Example 3

Treating Diabetes with the Disclosed Therapeutic Cells in an Animal Model

Alginate Encapsulation: Differentiated planar cultures of SR1423 were manually released using a cell lifter and rocked overnight at 95 RPM in a 6-well suspension culture dishes. Clusters formed were rinsed in 130 mM NaCl, 10 mM MOPS, pH 7.4 and re-suspended in 2% Pronova UP MVG alginate (Novamatrix) at a density of 2E6 cells/ml. Alginate/cell mixture was loaded into a syringe and either fed through a Nisco electrostatic droplet generator at 4ml/minute and 7 kV with a 0.24 um nozzle or manually dropped into a polymerization bath of 20 mM BaC12, 130 mM NaCl, 10 mM MOPS. Beads were rinsed four times and returned to differentiation media until transplant.

Induction of Diabetes in Mice: Immune-competent CD1 mice aged 8-10 weeks were used to induce diabetes with Streptozotocin (STZ, VWR # 102515-840). STZ was injected intraperitoneally (200 mg/kg) into the mice. STZ-induced diabetes was confirmed by measuring the blood glucose levels.

Figure 8:
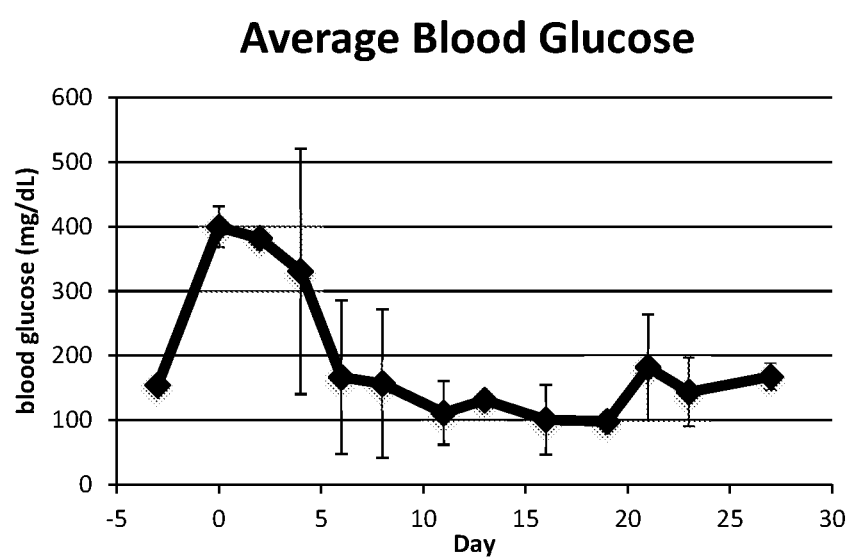
FIG. 8 shows reversal of diabetes in an animal model. Implanted cells regulate blood glucose after implant to streptozotocin-induced normal mice. Encapsulated cells were implanted on day 0. Results shown are the average of three mice. Error bars are standard deviation.

Transplantation of Alginate Encapsulated Differentiated SR1423 Cells: STZ induced diabetic mice were anesthetized with 20 mg/kg Tribromoethanol (Sigma # 776557888) and their abdomens shaved and sterilized with Isopropanol. A vertical incision was made in the middle of the abdomen below the sternum. Alginate beads were implanted to the peritoneum and the incision closed with sutures. Post-surgery, mice were given Ketoprofen (2.5 mg/Kg, ThermoFisher #P08D009) for 3 days. Mice were observed regularly after transplantation. Blood glucose levels were monitored twice per week by taking a small drop of blood from the tail vein using a commercial glucometer. Lower blood glucose was evident within 48 hours of transplant and was maintained for a period of weeks (FIG. 8).

Reversal of Diabetes in an animal model. A common method for immune-protecting islet cells for transplant is to embed the cells within alginate-containing microbeads. Surrogate pancreatic cells embedded within alginate and implanted to the peritoneum can demonstrate short-term reversal of diabetes and provides a good basis for a proof of concept. Microbeads formed of modified alginate with a lower tendency to stimulate fibrosis was able to reverse diabetes in normal rodents for up to 6 months. To demonstrate the ability of SR1423-generated cells to reverse diabetes within an immune-protective device, we embedded the differentiated cells within alginate beads and implanted these to the peritoneum of normal mice with chemically induced diabetes. Lower blood glucose was evident within 48 hours of transplant and was maintained for a period of weeks (FIG. 8).

Example 4

Culturing Non-Human Primate Cells Using the Disclosed Methods

The disclosed methods for isolating a pluripotent stem cell and efficiently differentiating the stem cell into an insulin-producing pancreatic lineage is also effective when beginning with non-human tissue, and beginning with non-pancreatic tissue. Fibroblast cells were harvested from skin biopsies of three non-human primates (NHP) of the species rhesus macaque and cultured identically as described for human cells (i.e., the culture and differentiation steps of Example 1). The reprogramming genes Oct4, Sox2, Klf4, and L-Myc were introduced to the primary fibroblast cells via electroporation of two episomal expression plasmids. The stem cell lines generated from the primary tissue of the NHP donors expressed the pluripotency markers Oct4, SSEA4, Tra-1-80, and Tra-1-60. These lines were screened for the ability to express endodermal markers after 4 days exposure to endoderm-inducing agents Activin-A and Wortmannin. Cultures with the highest proportion of cells expressing endodermal markers from each of the NHP donors were selected and subsequently screened for the ability to express pancreatic markers after exposure to a 12-day pancreatic differentiation protocol. The tissue from all three NHP donors yielded at least one stem cell line that efficiently generated pancreatic endodermal cells upon exposure to the described 12-day differentiation protocol. FIG. 9 shows a representative example of one of these lines derived from a NHP donor.

Example 5

Treating Diabetes in a Human Adult with the Disclosed Therapeutic Cells

This example illustrates methods of using the disclosed protocol to generate therapeutic cells to treat Type I diabetes in a human adult.

An adult human subject with insulin-dependent diabetes receives a transplant comprising a therapeutically effective amount of a composition comprising the disclosed macro-encapsulated insulin producing cells into the subject's omentum pouch or peritoneal cavity. The subject is evaluated for blood glucose levels. The subject is monitored following the implant of a therapeutically effective number of macro-encapsulated cells to ensure that the subject's blood glucose levels have been stabilized. The subject is further screened for glycosylated hemoglobin, and co-morbidities of diabetes over time.

What is claimed is:

1. A method of producing human insulin-secreting cells, comprising:
   (a) culturing human stem cells in adhesion, thereby allowing the human stem cells to spontaneously form three-dimensional structures, wherein the human stem cells are capable of differentiating into at least endodermal lineages; and
   (b) culturing the three-dimensional structures obtained in step (a) in suspension;
   wherein the culturing steps (a) and (b) comprise at least a 20-day exposure to retinoic acid and cyclopamine, and do not comprise exposing the three-dimensional structures to Wnt3A to obtain human insulin-secreting cells; and wherein the human stem cells are selected from embryonic stem cells, induced pluripotent stem cells, and multipotent reprogrammed stem cells.

2. The method of claim 1, wherein the human stem cells were derived from a cell line.

3. The method of claim 1, wherein the human stem cells are multipotent reprogrammed stem cells that were obtained by reprogramming human pancreatic cells.

4. The method of claim 3, wherein the multipotent reprogrammed stem cells were reprogrammed with expression plasmids encoding Oct4, Sox2, Klf4, and L-Myc.

5. The method of claim 3, wherein the multipotent reprogrammed stem cells were reprogrammed with expression plasmids encoding Oct4, Sox2, Klf4, and C-Myc.

6. The method of claim 3, wherein the multipotent reprogrammed stem cells were reprogrammed with expression plasmids encoding LIN28, Oct4, Sox2, and Nanog.

7. The method of claim 3, wherein the multipotent reprogrammed stem cells were reprogrammed with expression plasmids encoding Gils1, Oct3/4, Sox2, and Klf4.

* * * * *